(12) United States Patent
Bacallao et al.

(10) Patent No.: US 10,456,404 B2
(45) Date of Patent: Oct. 29, 2019

(54) TARGETING CGMP-RELATED PHOSPHODIESTERASES TO REDUCE CYST FORMATION IN CYSTIC KIDNEY DISEASE, AND RELATED MATERIALS AND METHODS

(71) Applicants: Indiana University Research and Technology Corporation, Indianapolis, IN (US); Rita Maria Cunha de Almeida, Porto Alegre (BR); United States Government as Represented by the Department of Veterans Affairs, Washington, DC (US)

(72) Inventors: Robert Bacallao, Indianapolis, IN (US); James A. Glazier, Bloomington, IN (US); Sherry G. Clendenon, Indianapolis, IN (US); Rita Maria Cunha De Almeida, Porto Alegre (BR)

(73) Assignees: Indiana University Research and Technology Corporation, Indianapolis, IN (US); United States Government as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 15/557,796

(22) PCT Filed: Mar. 14, 2016

(86) PCT No.: PCT/US2016/022377
§ 371 (c)(1),
(2) Date: Sep. 12, 2017

(87) PCT Pub. No.: WO2016/149218
PCT Pub. Date: Sep. 22, 2016

(65) Prior Publication Data
US 2018/0078559 A1    Mar. 22, 2018

Related U.S. Application Data

(60) Provisional application No. 62/132,724, filed on Mar. 13, 2015.

(51) Int. Cl.
| | |
|---|---|
| *A61K 31/4985* | (2006.01) |
| *C12Q 1/44* | (2006.01) |
| *G01N 33/68* | (2006.01) |
| *A61K 31/53* | (2006.01) |
| *C12Q 1/6883* | (2018.01) |
| *A61K 31/519* | (2006.01) |
| *A61K 45/06* | (2006.01) |

(52) U.S. Cl.
CPC .......... *A61K 31/53* (2013.01); *A61K 31/4985* (2013.01); *A61K 31/519* (2013.01); *A61K 45/06* (2013.01); *C12Q 1/44* (2013.01); *C12Q 1/6883* (2013.01); *G01N 33/6893* (2013.01); *C12Q 2600/106* (2013.01); *C12Q 2600/158* (2013.01); *G01N 2333/916* (2013.01); *G01N 2800/347* (2013.01)

(58) Field of Classification Search
CPC . A61K 31/519; G01N 1/6883; G01N 33/6893
USPC ........................................................ 514/252
See application file for complete search history.

(56) References Cited

U.S. PATENT DOCUMENTS

| | | |
|---|---|---|
| 2003/0008288 A1 | 1/2003 | Germino et al. |
| 2011/0229895 A1 | 9/2011 | Walz |
| 2012/0252816 A1* | 10/2012 | Chen .................... A61K 31/277 514/243 |
| 2012/0269898 A1 | 10/2012 | Belardinelli et al. |
| 2013/0338137 A1 | 12/2013 | Follmann et al. |

FOREIGN PATENT DOCUMENTS

| | | |
|---|---|---|
| EP | 953357 A | 11/1999 |
| EP | 0953357 A1 | 11/1999 |
| WO | 2008137318 A1 | 11/2008 |

OTHER PUBLICATIONS

International Search Report and Written Opinion issued by the ISA/US, Commissioner for Patents, dated Jun. 30, 2016, for International Application No. PCT/US2016/022377; 8 pages.
Brown, Kayleigh E. et al., "Potential Therapeutic Role of Phosphodiesterase Type 5 Inhibition in Hypertension and Chronic Kidney Disease," *Hypertension*, Jan. 2014; 63:5-11, original published online Oct. 7, 2013, retrieved from the Internet on Aug. 31, 2017 http://hyper_ahajournals.org/content/63/1/5, 2017; 15 pages.
International Preliminary Report on Patentability issued by The International Bureau of WIPO, dated Sep. 19, 2017, for International Application No. PCT/US2016/022377; 7 pages.
Partial Supplementary European Search Report issued by the European Patent Office, Munich, Germany, dated Oct. 18, 2018, for European Patent Application No. 16765568.7.
Extended European Search Report issued by the European Patent Office, Munich, Germany, dated Jan. 19, 2019, for European Patent Application No. 16765568.7.
Cheng, Jingfei et al., "Cyclic Nucleotide Phosphodiesterase (PDE) Inhibitors: Novel therapeutic Agents for Progressive Renal Disease," Experimental Biology and Medicine, vol. 232, No. 1, Jan. 1, 2007.

(Continued)

*Primary Examiner* — Raymond J Henley, III
(74) *Attorney, Agent, or Firm* — Faegre Baker Daniels LLP

(57) ABSTRACT

Described herein is the identification of cGMP-specific phosphodiesterase upregulation in cystic kidney diseases. Also described is the use of cGMP-specific phosphodiesterase inhibitors for preventing the progression and/or treatment of cystic kidney diseases. Other aspects described provide medicaments for preventing the progression and/or treating cystic kidney diseases, and methods of diagnosing cystic kidney disease.

20 Claims, 10 Drawing Sheets
(6 of 10 Drawing Sheet(s) Filed in Color)

(56) References Cited

OTHER PUBLICATIONS

Wang, Xiaofang et al., "Cyclic nucleotide signaling in polycystic kidney disease," Kidney International, (2010), vol. 77, No. 2.
De Almeida, Rita M.C., et al., "Transcriptome analysis reveals manifold mechanisms of cyst development in ADPKD," Human Genomics, Biomed Central Ltd., London, UK, vol. 10, No. 1, Nov. 21, 2016.

* cited by examiner

Control 1:250

Sildenafil treated 1:250

Control 1:500

Sildenafil treated 1:500

TARGETING CGMP-RELATED PHOSPHODIESTERASES TO REDUCE CYST FORMATION IN CYSTIC KIDNEY DISEASE, AND RELATED MATERIALS AND METHODS

CROSS-REFERENCE TO RELATED APPLICATIONS

This application is the U.S. National Stage Application of International Patent Application No. PCT/2016/022377, filed Mar. 14, 2016, which claims the benefit of U.S. Provisional Patent Application No. 62/132,724, filed Mar. 13, 2015, each of which is expressly incorporated herein by reference in its entirety.

BACKGROUND

Renal cysts occur in a variety of conditions, and are the most common genetic cause of end-stage renal disease (ESRD). Despite being a major clinical concern and many of the genes causing cystic disease have been identified, knowledge of the molecular nature of the mutations has not been able to clarify the mechanism underlying cyst formation.

Renal cysts may result due to genetic disorders, non-genetic developmental disorders, and non-genetic acquired disorders. Autosomal dominant polycystic kidney disease (ADPKD) is the most common kidney cyst disease, and is among the most common inherited human diseases. With intrarenal cystogenesis as its primary characteristic, its prevalence is 1 in 400 to 1 in 1,000. Of affected families, 85% have mutations in PKD1 (located on the short arm of chromosome 16), which encodes Polycystin 1, while the rest have mutations in PKD2 (located on the long arm of chromosome 4), which encodes Polycystin 2. Individuals with PKD2 mutations generally present later and have a slower rate of progression to ESRD than individuals with PKD1 mutations. Cysts in ADPKD can arise from any part of the nephron as outpouchings connected to the tubular lumen, which eventually disconnect. Over time, they enlarge, destroying normal parenchyma, resulting in bilateral kidney enlargement, and culminating in kidney failure.

Most patients present between 20-40 years of age, although early onset (under 15 years of age) and very early onset (less than 2 years of age, even in utero) ADPKD does occur. Common renal symptoms include abdominal pain, polyuria, urinary tract infections, hematuria, and hypertension. Hepatic, pancreatic, ovarian, splenic, and intestinal diverticula may also occur.

At present, treatment options for cystic kidney disease comprise symptom management including pain management, blood pressure management, antibiotics to treat uterine tract infections, and diuretics to help remove excess fluid, and dialysis or kidney transplant. These options, particularly dialysis and transplant, are expensive and can negatively affect a patient's quality of life.

SUMMARY

Described herein is the identification of cGMP-specific phosphodiesterase upregulation in cystic kidney diseases. Also described is the use of cGMP-specific phosphodiesterase inhibitors for preventing the progression and/or treatment of cystic kidney diseases. Other aspects described provide medicaments for preventing the progression and/or treating cystic kidney diseases, and methods of diagnosing cystic kidney disease.

In a particular embodiment described herein is a method for preventing the progression of and/or treating a cystic kidney disease in a subject in need thereof, comprising administering an effective amount of at least one phosphodiesterase inhibitor to the subject, wherein the phosphodiesterase inhibitor inhibits at least one phosphodiesterase selected from the group consisting of: phosphodiesterase type 5; phosphodiesterase type 6; and phosphodiesterase type 9. In certain embodiments, the at least one phosphodiesterase inhibitor is selected from the group consisting of: sildenafil; aildenafil; tadalafil; vardenafil; udenafil; avanafil; lodenafil; mirodenafil; dipyridamole; icariin; zaprinast; PF-04447943; BAY 73-6691; a pharmaceutically acceptable salt of sildenafil, aildenafil, tadalafil, vardenafil, udenafil, avanafil, lodenafil, mirodenafil, dipyridamole, icariin, zaprinast, PF-04447943, or BAY 73-6691; a hydrate of the pharmaceutically acceptable salt of sildenafil, aildenafil, tadalafil, vardenafil, udenafil, avanafil, lodenafil, mirodenafil, dipyridamole, icariin, zaprinast, PF-04447943, or BAY 73-6691; a pharmaceutically effective prodrug of sildenafil, aildenafil, tadalafil, vardenafil, udenafil, avanafil, lodenafil, mirodenafil, dipyridamole, icariin, zaprinast, PF-04447943, or BAY 73-6691; and a pharmaceutically active metabolite of sildenafil, aildenafil, tadalafil, vardenafil, udenafil, avanafil, lodenafil, mirodenafil, dipyridamole, icariin, zaprinast, PF-04447943, or BAY 73-6691.

In an embodiment described herein, the cystic kidney disease is a polycystic kidney disease selected from the group consisting of: autosomal dominant polycystic kidney disease; and autosomal recessive polycystic kidney disease.

A subject as described in any one of the embodiments described herein may be an individual selected from the group consisting of: human; feline; canine; equine; cattle; swine; sheep; and goat.

In another particular embodiment described herein is a medicament for preventing the progression of and/or treating a cystic kidney disease, comprising at least one phosphodiesterase inhibitor, wherein the phosphodiesterase inhibitor inhibits at least one phosphodiesterase selected from the group consisting of: phosphodiesterase type 5; phosphodiesterase type 6; and phosphodiesterase type 9, and one or more pharmaceutically acceptable liquid carriers, solid carriers, vehicles, and/or excipients.

In certain embodiments described herein, the medicament further comprises a kidney-targeted drug delivery system. The kidney-targeted drug delivery system may be of a type selected from the group consisting of: lysozyme; low molecular weight chitosan; poly(vinylpyrrolidone-co-dimethyl maleic acid); G3-C12 peptide; sugar-modified prodrugs; amino acid-modified prodrugs; folate-modified prodrugs; nanoparticles; and liposomes.

In another particular embodiment described herein is a method for diagnosing a cystic kidney disease in a subject, the method comprising measuring expression levels in a renal test sample obtained from the subject at least one gene product of a cGMP-related phosphodiesterase gene selected from the group of phosphodiesterase type 5, phosphodiesterase type 6, and phosphodiesterase type 9; and comparing the expression levels of the at least one gene product against a control expression value to determine whether the expression levels of the at least one gene product are elevated as compared to the control expression value. In certain embodiments, the renal test sample is a renal cell sample or renal tissue sample.

In certain embodiments described herein, the control expression value is an average expression value of the measured at least one gene product of a cGMP-related phosphodiesterase gene in a population of healthy subjects. The population of healthy subjects can be of a size selected from the group consisting of: an individual subject; at least 5 subjects; at least 10 subjects; at least 20 subjects; at least 50 subjects; and at least 100 subjects.

In other embodiments described herein, the levels of phosphodiesterase type 5, phosphodiesterase type 6, and phosphodiesterase type 9 gene expression are significantly higher than those found in cell and/or tissue samples from a population of healthy subjects, indicating cystic kidney disease, wherein significance is determined by t-test, wherein $p<0.05$.

In certain embodiments, gene expression is determined using quantitative RT-PCR analysis or microarray analysis.

In another particular embodiment, at least one cGMP-specific phosphodiesterase inhibitor, or a pharmaceutically acceptable salt thereof, or a hydrate of the pharmaceutically acceptable salt thereof, or a pharmaceutically effective prodrug thereof, or a pharmaceutically active metabolite thereof, is described for use in a method to prevent the progression of and/or treat a cystic kidney disease in a subject in need thereof, the method comprising a safe and effective amount of the at least one cGMP-specific phosphodiesterase inhibitor, or a pharmaceutically acceptable salt thereof, or a hydrate of the pharmaceutically acceptable salt thereof, or a pharmaceutically effective prodrug thereof, or a pharmaceutically active metabolite thereof, to the patient in need thereof.

BRIEF DESCRIPTION OF THE DRAWINGS

The patent or application file contains at least one drawing executed in color. Copies of this patent or patent application with color drawings will be provided by the Office upon request and payment of the necessary fee.

DETAILED DESCRIPTION

Described herein is the identification of cGMP-specific phosphodiesterase upregulation in cystic kidney diseases. Also described herein is the use of cGMP-specific phosphodiesterase inhibitors for preventing the progression and/or treatment of cystic kidney diseases. Other aspects described herein provide medicaments for preventing the progression and/or treating cystic kidney diseases, and methods of diagnosing cystic kidney disease.

Renal cysts occur in a variety of conditions, and are the most common genetic cause of end-stage renal disease (ESRD). Despite being a major clinical concern, and many of the genes causing cystic disease have been identified, knowledge of the molecular nature of the mutations has not been able to clarify the mechanism underlying cyst formation.

Described herein for the first time is the finding that phosphodiesterase (PDE) types 5, 6, and 9 (PDE5, PDE6, and PDE9, respectively) are upregulated in cystic kidney tissue. Using transcriptogram analysis, a powerful, sensitive method to analyze gene expression data, all cystic kidney tissues tested showed significant upregulation of these three PDEs (PDE5, PDE6, and PDE9). Inhibition of these PDEs, which are all cGMP-specific phosphodiesterases, is shown herein to reduce average renal cyst size and prevent renal cyst growth.

Figure 1:
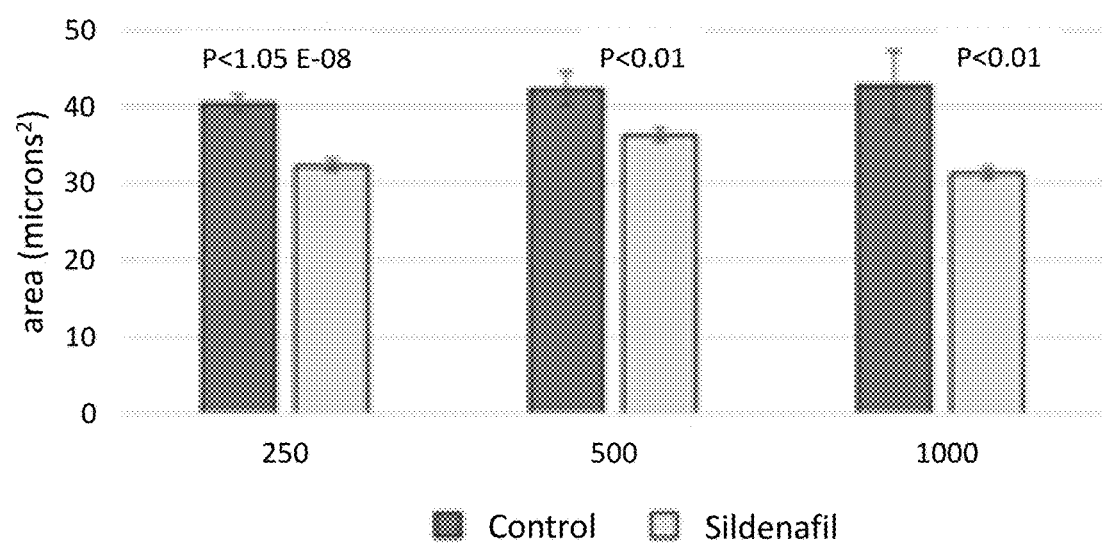
FIG. 1: Sildenafil citrate (sold under the trade name Viagra®) treatment reduced average cyst size in culture. Cells were treated with 250, 500, or 1000 ng/ml sildenafil citrate. The depicted bar graph shows that in vitro cyst formation is reduced by treatment with sildenafil citrate at all concentrations tested

As shown in FIG. 1, treatment of cyst structures grown from immortalized polycystic kidney cells with sildenafil citrate (sold under the trade name Viagra®) resulted in significant reductions in average cyst size. Dosages of 250 ng/ml, 500 ng/ml, and 1,000 ng/ml were tested, with no dose response observed, indicating that lower concentrations will also be effective at reducing average cyst size.

Figure 2:
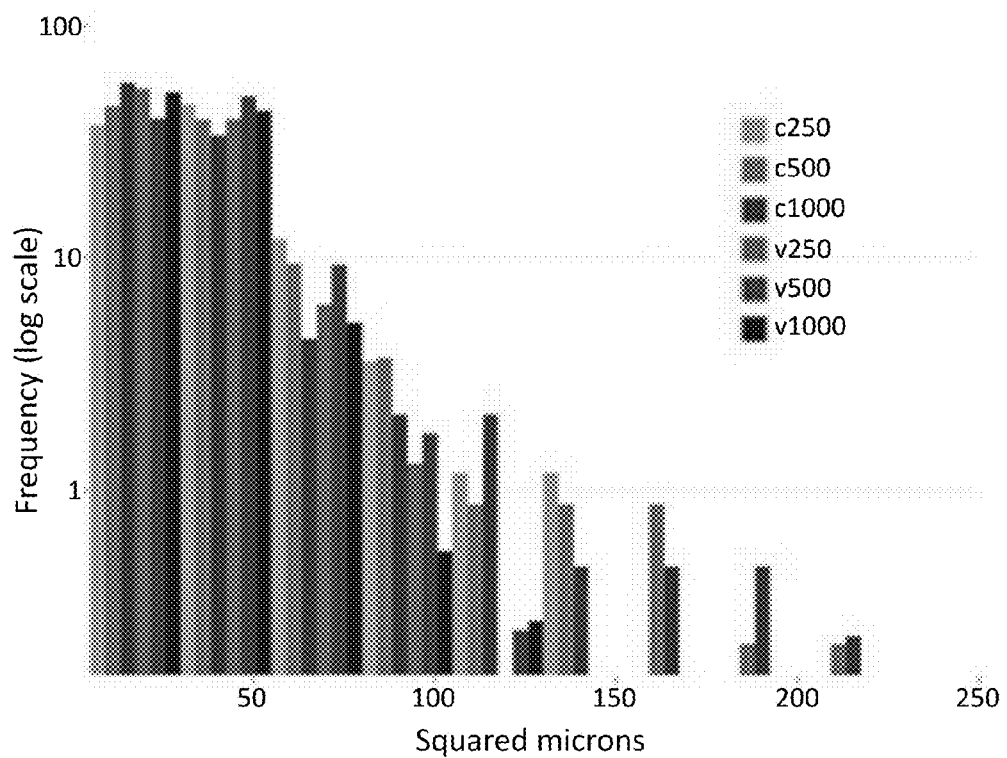
FIG. 2: Large cysts are absent from sildenafil citrate (sold under the trade name Viagra®) treated cultures. Cells were treated with 250, 500, or 1000 ng/ml sildenafil citrate (noted as v250, v500, and v1000, respectively), or sham-treated with matched controlled with vehicle but no drug (noted as c250, c500, and c1000, respectively). The frequency distribution bar graph shows average cyst size being reduced by treatment with sildenafil citrate, as evidence by the absence of large cysts in sildenafil citrate treated cultures.

Frequency distribution analysis, depicted in FIG. 2, shows that treatment of cyst structures grown from immortalized polycystic kidney cells with sildenafil citrate results in the absence of large cysts, indicating that sildenafil citrate inhibits the progression of cyst formation. The depicted frequency distribution, which indicates the frequency of cysts of designated size, indicates that while large cyst structures of greater than $150\mu^2$ continued to form in vehicle-treated control cells, treatment with sildenafil citrate completely inhibited large cyst formation. These results demonstrate the ability of cGMP-specific PDE inhibitors to reduce average renal cyst size and prevent renal cyst growth.

Figure 3A:
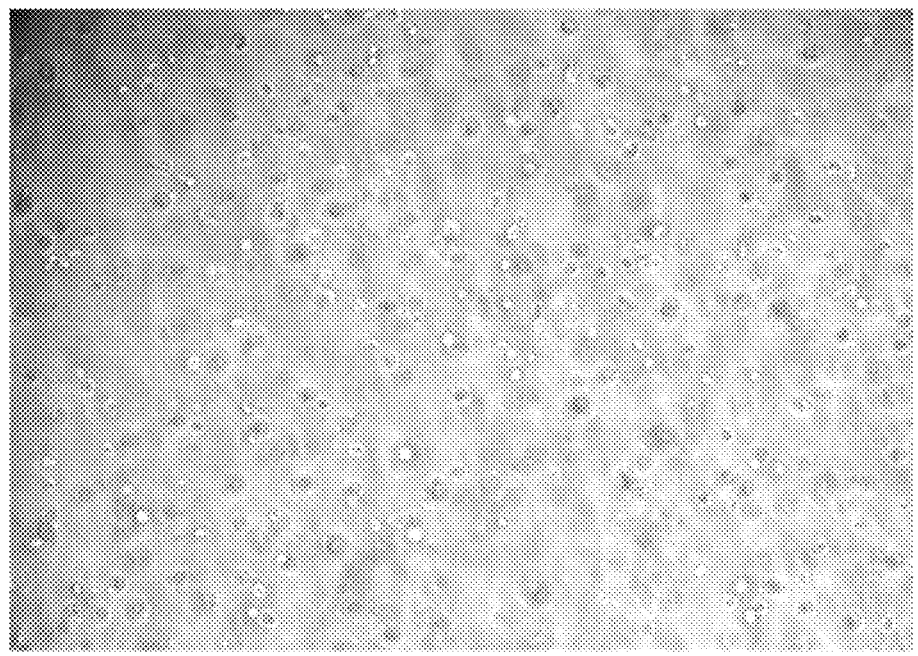
FIG. 3A: Photograph of control cells for the 1:250 sildenafil treated group depicted in FIG. 3B. Image collected with a 20× phase contrast objective.
Figure 3B:
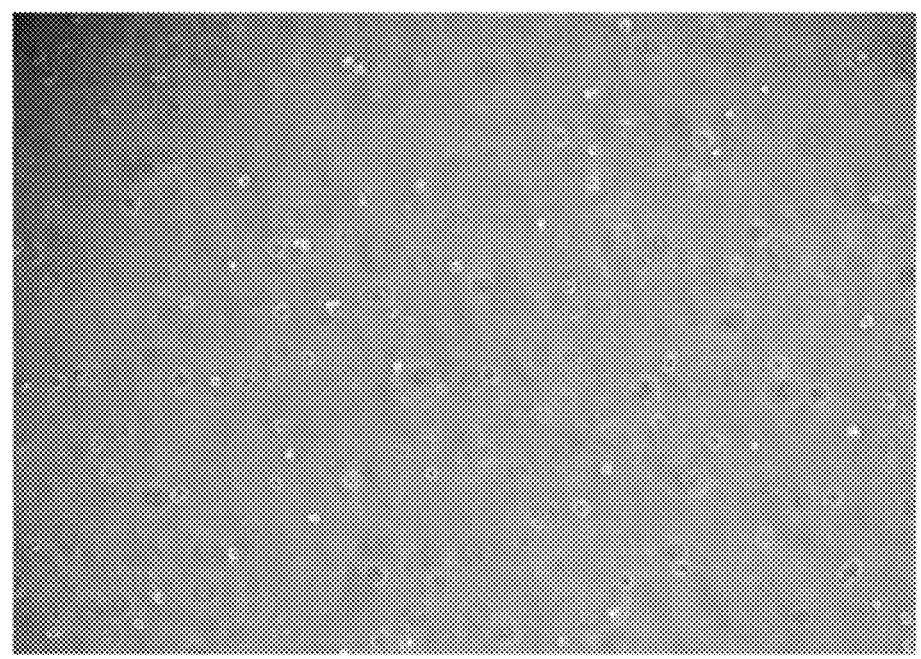
FIG. 3B: Photograph of cells treated with a 1:250 sildenafil dilution of drug in vehicle from a stock. Image collected with a 20× phase contrast objective.

FIGS. 3A-3B present photographs of control treatment (FIG. 3A) or cells treated with a 1:250 dilution of sildenafil in vehicle from a stock (FIG. 3B). No large cysts were observed in the sildenafil treated group. Images were collected with a 20× phase contrast objective.

Figure 4A:
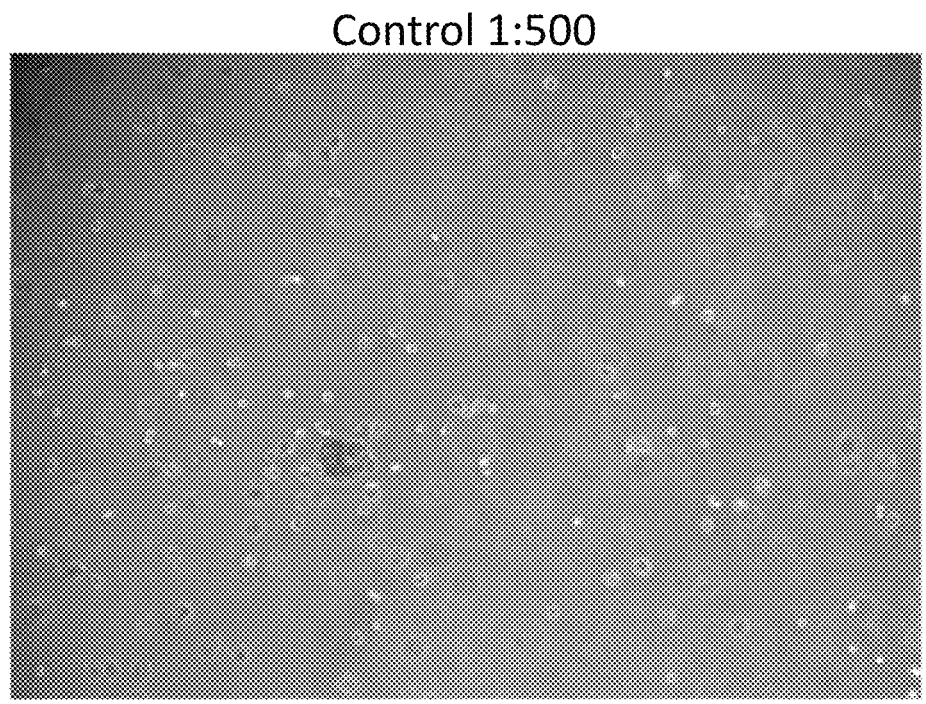
FIG. 4A: Photograph of control cells for the 1:500 sildenafil treated group depicted in FIG. 4B. Image collected with a 20× phase contrast objective.
Figure 4B:
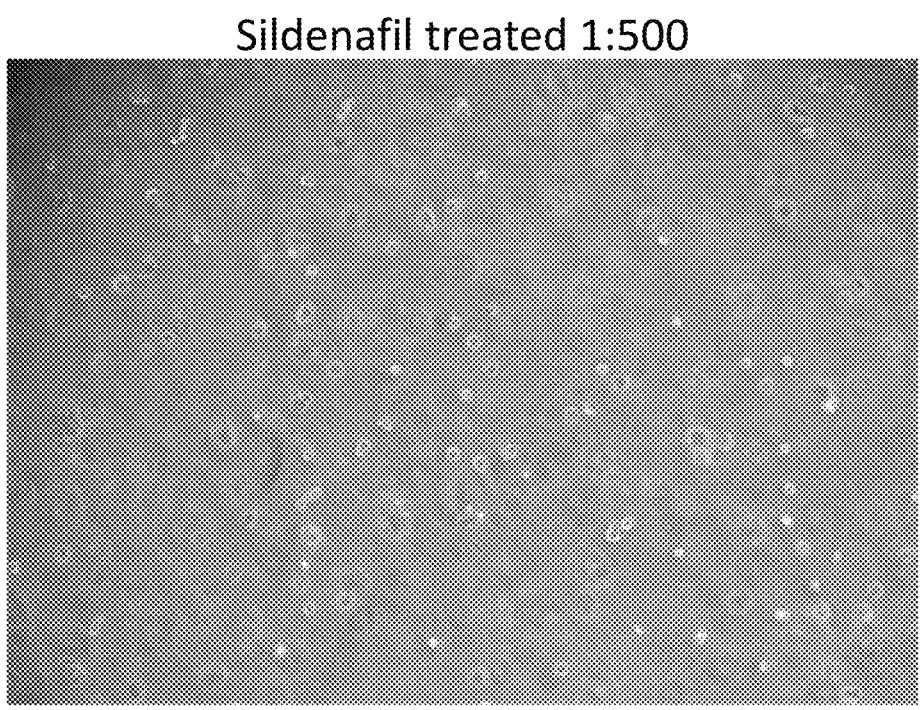
FIG. 4B: Photograph of cells treated with a 1:500 sildenafil dilution of drug in vehicle from a stock. Image collected with a 20× phase contrast objective.

FIGS. 4A-4B present photographs of control treatment (FIG. 4A) or cells treated with a 1:500 dilution of sildenafil in vehicle from a stock (FIG. 4B). No large cysts were observed in the sildenafil treated group. Images were collected with a 20× phase contrast objective.

Figure 5A:
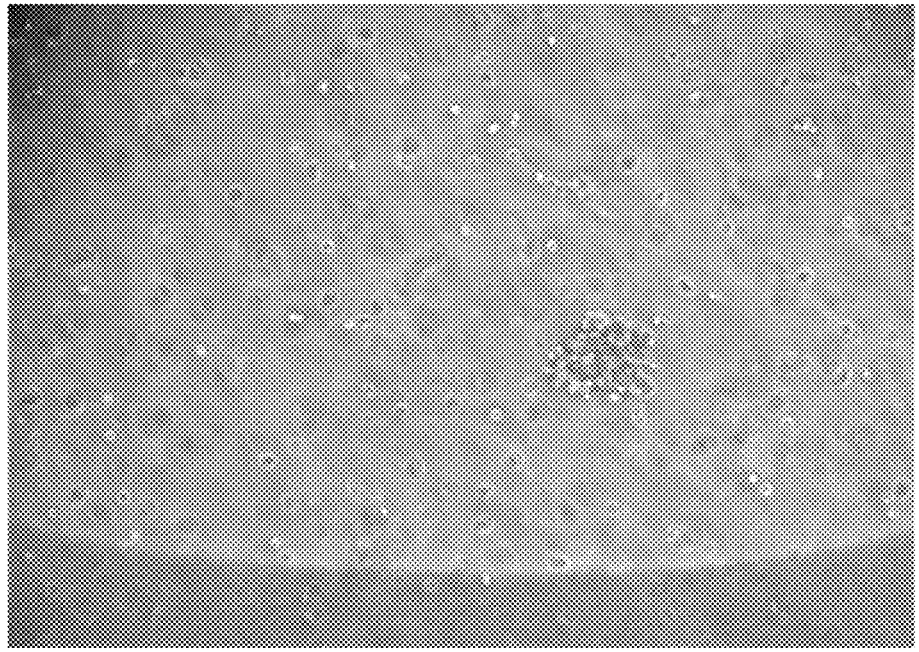
FIG. 5A: Photograph of control cells for the 1:1000 sildenafil treated group depicted in FIG. 3B. Image collected with a 20× phase contrast objective.
Figure 5B:
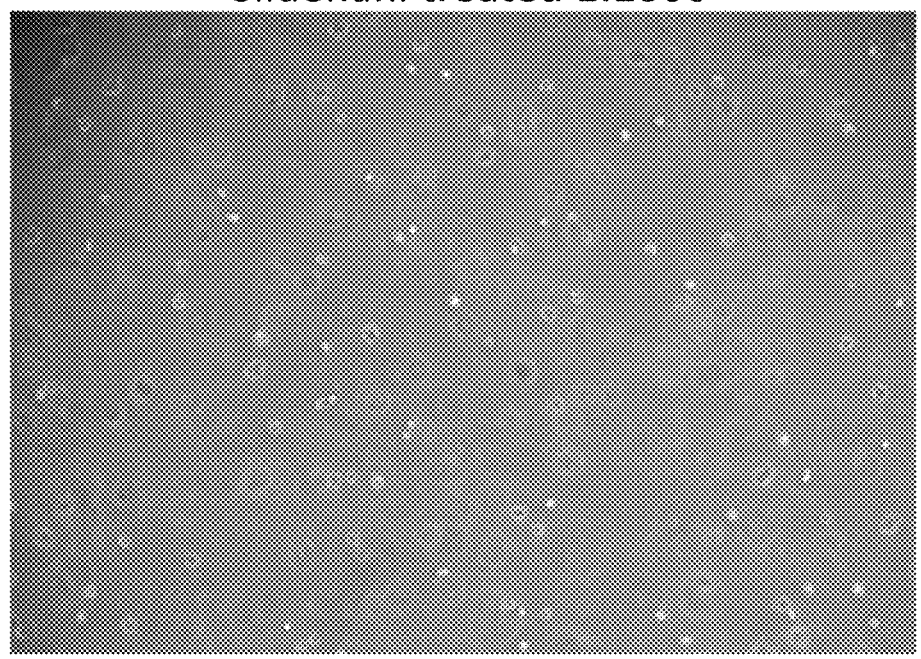
FIG. 5B: Photograph of cells treated with a 1:1000 sildenafil dilution of drug in vehicle from a stock. Image collected with a 20× phase contrast objective.

FIGS. 5A-5B present photographs of control treatment (FIG. 5A) or cells treated with a 1:1000 dilution of sildenafil in vehicle from a stock (FIG. 5B). No large cysts were observed in the sildenafil treated group. Images were collected with a 20× phase contrast objective.

Transcriptogram Analysis

Due lack of understanding regarding the mechanism that links polycystic kidney disease (PKD) mutations (e.g., mutations of PKD1 and/or PKD2 in autosomal dominant polycystic kidney disease (ADPKD)) and the cell behavior changes that drive cyst formation, transcriptogram analysis was utilized to identify target molecular pathways involved in renal cyst development.

Transcriptogram analysis, first described by Rybarczyk-Filho et al. (*Nucleic Acids Res.*, 39(8): 3005-15 (2011); incorporated by reference herein in its entirety), is a powerful and sensitive computational method to analyze gene expression data and identify affected pathways. The method comprises ordering genes on a line and clustering the genes by the probability that their products interact. Protein-protein association information can be obtained from large databases, such as STRING. The genome organization obtained this way is independent from specific experiments, and defines functional modules that are associated with gene ontology terms. The starting point is a gene list and a matrix specifying interactions.

Genome-wide expression data consist of expression levels of thousands of genes. The joint analysis of the whole data represents a significant challenge. The usual approaches compare expression levels of modified cellular stages relative to those of a pre-established control. The genes are then ranked by the variations in expression relative to the control and those genes that present the most significant alterations (highest or lowest) are chosen to be further analyzed. However, genes have their expression dynamics determined by a network of other genes, and moderate alterations on many interacting genes may cause measurable effects on cell metabolism. These effects may be overlooked when using the maximally altered level criterion but, on the other hand, the great amount of data may prevent a more accurate analysis.

The transcriptogram approach produces 'images' of gene expression data of whole genomes, by producing expression profiles for transcriptomes. The basis of the method is to consider averages of expression data over neighboring genes disposed on a line, as in the metaphoric example of the high-resolution photograph. On one hand, this procedure targets a global assessment of expression data of whole genomes. On the other hand, it requires the definition of gene neighborhood when disposed on a line, which is not straightforward.

Expression levels of different genes may differ by large amounts. Consequently, a random list of genes generates plots of relative gene expression levels that fluctuate so wildly that very little information, if any, can be gathered from them. Techniques to extract information from wildly fluctuating general profiles consider averages taken over intervals of neighboring points. In the case where genes are ordered on a list following some criterion that favors clustering together interacting genes, the distance between any two genes on the list may correlate with the probability of mutual interaction, yielding then a natural criterion to define gene neighborhood on the list.

Many algorithms exist that find clusters of nodes in complex networks. These algorithms have been successfully applied to gene networks based on protein-protein interactions. However, they do not order genes on a list, but rather present the genes that belong to the same cluster in an arbitrary order. An exception is the clustering algorithm proposed by Barabási and collaborators (Ravasz et al., *Science*, (2002) 297, 1551; Barabási and Oltavai, *Nat. Rev. Genet.*, (2004)). Also, analysis of trancriptomes often cluster together genes by their co-expression, or co-variation in time, which implies that these cluster definitions depend on the stage the cell is going through or on the protocol used to produce the assessed sample.

The transcriptogram method described by Rybarczyk-Filho et al. (2011) orders a list of genes using the computational physics method known as Monte Carlo. The aim is to cluster on a line interacting genes, such that the distance between two genes on the list correlates with the probability that they interact, that is, the probability that their protein products are associated in protein-protein association data bases such as STRING. A first advantage is that the definition of these clusters is independent from the specific stage the cells are at a given moment, or the protocol they have suffered. The genome ordering of Rybarczyk-Filho et al. (2011) defines a mathematical metric that correlates the distance between two genes on the list with their mutual influence. The probability that two genes interact decreases with the distance between their localization on the ordered list, and an average of the expression levels over neighboring genes on this list dumps fluctuations and produces a smooth profile termed a 'transcriptogram'. The ordering is capable of clustering together genes belonging to gene ontology terms of Gene Ontology: Biological Processes (The Gene Ontology Consortium, *Nat. Genet.*, (2000) 25, 29). Furthermore, expression profiles projected on the ordering give enough information on the global performance of a cell to discriminate different metabolic or biosynthetic processes, rendering a global assessment of cellular metabolism.

Relative transcriptograms for cystic kidney tissues, including ADPKD tissues, were calculated using published data (Song et al., *Hum. Molec. Genet.*, (2009) 18(13), 2328). As described in Song et al., all cystic tissues differed from control but not from each other. The present transcriptogram analysis revealed changes in genes associated with translation and DNA repair, Notch, Wnt, and transmembrane receptor tyrosine kinase signaling pathways. The present transcriptogram analysis also detected changes in minimally cystic tissues that were not detected by standard microarray analysis, including genes associated with the cytoskeleton, integrins, cell adhesion, mitochondria, and retinol metabolism. Differences were also identified in G-protein signaling and phosphodiesterase pathways.

A particular group of phosphodiesterases that degrade cGMP were found by the present transcriptogram analysis to be upregulated in every type of cystic kidney tissue examined. The upregulated cGMP-related PDEs included PDE5, PDE6, and PDE9. These PDEs have not previously been identified in cystic kidney diseases, and were investigated as therapeutic targets.

Phosphodiesterases

The 3',5'-cyclic nucleotide phosphodiesterases (PDEs), which hydrolyze the intracellular second messengers cAMP and cGMP to their corresponding monophosphates, play an important role in signal transduction by regulating the intracellular concentration of cyclic nucleotides. Numerous cellular functions are regulated by these second messengers. In the cardiovascular system, blood pressure is regulated by contraction and relaxation of vascular smooth muscle in association with vascular endothelial functions. Beating of cardiac myocytes is accurately controlled to pump blood out of the heart to other parts of the body according to environmental conditions. These events in hemodynamics are regulated by extracellular stimulation through alteration of intracellular cyclic nucleotide levels, which are determined by a balance between their production and degradation by PDEs. Downstream effector proteins of cAMP and cGMP are cAMP-dependent protein kinase (PKA), cGMP-dependent protein kinase (PKG), cyclic nucleotide-gated ion channels, and cAMP-regulated guanine nucleotide exchange factors (cAMP-GEFs), which are also called exchange proteins directly activated by cAMP (Epacs). PDEs are also downstream effectors of cAMP and cGMP. Studies on cyclic nucleotide-mediated signaling have revealed that the signal for each physiological event is independently regulated by compartmentation of certain signaling molecules. PDEs are closely related to the regulation of each specific transduction signal, and therefore multiple PDEs play important roles in modulating each cellular function. Previously, PDEs had not been associated with renal cyst formation.

PDEs comprise a large class of enzymes divided into at least eleven different families which are structurally, biochemically and pharmacologically distinct from one another. The enzymes within each family are commonly referred to as isoenzymes, or isozymes. Further diversity among the isoenzymes results from differential splicing and post-translational processing of those gene products.

PDE5 Inhibitors

Many cGMP-specific PDE inhibitors are known in the art. PDE5 inhibitors, which generally also inhibit PDE6 and PDE9 with varying efficacy, are most famously prescribed for the treatment of erectile dysfunction, but have been also demonstrated to be useful in reducing symptoms of pulmonary hypertension and commencing right-heart failure (Michelakis et al., *Circulation*, (2003) 108, 2066; Ghofrani et al., *J. Am. Coll. Cardiol.*, (2003) 42, 158; Ghofrani et al. *Lancet*, (2002) 360, 895; Ghofrani et al., *AJRCCM*, (2003) 167(8), 1139). PDE5 inhibitors have also been shown to have many other effects, including: inducing neurogenesis and promoting functional recovery after stroke in rats (Zhang et al., *Stroke*, (2002) 33, 2675; Zhang et al., *Circ. Res.*, (2003) 92(3), 308); relaxing epicardial coronary arteries of patients with coronary artery disease (Halcox et al., *J. Am. Coll. Cardiol.*, (2002) 40, 1232); working in diabetic gastropathy in some animal studies, in which nNOS and activity were reduced (Watkins et al., *J. Clin. Invest.*, (2000) 106, 373); improving the spatial balance between blood perfusion and ventilation in COPD (WO 03/051346); and treating sepsis-associated encephalopathy (U.S. Pat. No. 8,278,300).

Compounds which can be used to inhibit PDE5 include but are not limited to 3-ethyl-8-[2-(4-morpholinylmethyl) benzylamino]-2,3-dihydro-1H-imidazo[4,5-g]quinazoline-2-thione, 1-(2-chlorobenzyl)-3-isobutyryl-2-propylindole-6-carboxamide, 9-bromo-2-(3-hydroxypropoxy)-5-(3-pyridylmethyl)-4H-pyrido[3,2,1-jk]-carbazol-4-one, 4-(1,3-benzodioxol-5-ylmethylamino)-2-(1-imidazolyl)-6-methylthieno[2,3-d]pyrimidine, 6-(2-isopropyl-4,5,6,7-terahydropyrazolo[1,5-a]pyridin-3-yl)-5-methyl)-5-methyl-2,3,4,5-tetrahydropyridazin-3-one, 5-(4-methylbenzyl)-3-(1-methyl-4-phenylbutyl)-3,6-dihydro-[1,2,3]triazolo[4,5-d]pyrimidin-7-one, 3-(1-methyl-4-phenylbutyl)-5-pyridin-4-ylmethyl-3,6-dihydro-[1,2,3]triazolo[4,5-d]pyrimidin-7-one, 5-(4-bromobenzyl)-3-(1-methyl-4-phenylbutyl)-3,6-dihydro-[1,2,3]triazolo[4,5-d]pyrimidin-7-one, 5-benzyl-3-(1-methyl-4-phenylbutyl)-3,6-dihydro-[1,2,3]triazolo[4,5-d]pyrimidin-7-one, 5-(3,4-dimethoxybenzyl)-3-(1-methyl-4-phenylbutyl)-3,6-dihydro-[1,2,3]triazolo-[4,5-d]pyrimidin-7-one, 5-(3,4-dichlorobenzyl)-3-(1-methyl-4-phenylbutyl)-3,6-dihydro-[1,2,3]triazolo[4,5-d]pyrimidin-7-one, 5-biphenyl-4-ylmethyl-3-(1-methyl-4-phenylbutyl)-3,6-dihydro-[1,2,3]triazolo[4,5-d]pyrimidin-7-one, 5-(4-aminobenzyl)-3-(1-methyl-4-phenylbutyl)-3,6-dihydro-[1,2,3]triazolo[4,5-d]pyrimi-din-7-one, 5-(hydroxyphenylmethyl)-3-(1-methyl-4-phenylbutyl)-3,6-dihydro-[1,2,3]triazolo-[4,5-d]pyrimidin-7-one, 5-benzo[1,3]dioxol-5-ylmethyl-3-[1-methyl-4-phenylbutyl]-3,6-dihydro-[1,2,3]triazolo[4,5-d]pyrimidin-7-one, N-4-[3-(1-methyl-4-phenylbutyl)-7-oxo-6,7-dihydro-3H-[1,2,3]triazolo-[4,5-d]pyrimidin-5-ylmethyl]phenylacetamide, 5-benzoyl-3-(1-methyl-4-phenylbutyl)-3,6-dihydro-[1,2,3]triazolo[4,5-d]-pyrimidin-7-one, 3-(1-methyl-4-phenylbutyl)-5-[4-(morpholine-4-sulphinyl)benzyl]-3,6-dihydro[1,2,3]triazolo[4,5-d]pyrimidin-7-one, 3-(1-methyl-4-phenylbutyl)-5-[3-(morpholine-4-sulphonyl)benzyl]-3,6-dihydro[1,2,3]triazolo[4,5-d]pyrimidin-7-one, N-methyl-4-[3-(1-methyl-4-phenylbutyl)-7-oxo-6,7-dihydro-3H-[1,2,3]-triazolo-[4,5-d]pyrimidin-5-ylmethyl]-benzenesulphonamide, N-(2-dimethylaminoethyl)-4-[3-(1-methyl-4-phenylbutyl)-7-oxo-6,7-dihydro-3H-[1,2,3] triazolo[4,5-d]pyrimidin-5-ylmethyl]benzenesulphonamide, N-(2-hydroxyethyl)-4-[3-(1-methyl-4-phenylbutyl)-7-oxo-6,7-dihydro-3H-[1,2,3]triazolo[4,5-d]pyrimidin-5-ylmethyl]benzenesulphonamide, ethyl 1-[3-[3-(1-methyl-4-phenylbutyl)-7-oxo-6,7-dihydro-3H-[1,2,3]-triazolo-[4,5-d]

pyrimidin-5-ylmethyl]benzenesulphonyl]piperidinecarboxylate, 3-(1-methyl-4-phenylbutyl)-5-[4-(4-methylpiperazin-1-sulphonyl)benzyl]-3,6-dihydro-[1,2,3]triazolo[4,5-d]pyrimidin-7-one, 5-benzo[1,3]dioxol-5-ylmethyl-3-[1-ethyl-heptyl]-3,6-dihydro-[1,2,3]-triazolo[4,5-d]pyrimidin-7-one, 3-[1-(1-hydroxyethyl)-4-phenylbutyl]-5-[4-(morpholine-4-sulphonyl)benzyl]-3,6-dihydro-[1,2,3]triazolo[4,5-d]pyrimidin-7-one, 5-[6-fluoro-1-(phenylmethyl)-1H-indazol-3-yl]-2-furanmethanol, 1-benzyl-6-fluoro-3-[5-(hydroxymethyl)furan-2-yl]-1H-indazole, 2-(1H-imidazol-1-yl)-6-methoxy-4-(2-methoxyethylamino)quinazoline, 1-[[3-(7,8-dihydro-8-oxo-1H-imidazo[4,5-g]quinazolin-6-yl)-4-propoxyphenyl]sulphonyl]-4-methylpiperazine, 4-(3-chloro-4-methoxybenzylamino)-1-(4-hydroxypiperidin-1-yl)phthalazine-6-carbonitrile, 1-[6-chloro-4-(3,4-methylendioxybenzylamino)quinazolin-2-yl]piperidin-4-carboxylic acid, (6R,12aR)-6-(1,3-benzodioxol-5-yl)-2-methyl-1,2,3,4,6,7,12,12a-octa-hydropyrazino[2',1':6,1]pyrido[3,4-b]indole-1,4-dione (tadalafil), (6R,12aR)-2,3,6,7,12,12a-hexahydro-2-methyl-6-(3,4-methylenedioxyphenyl)-pyrazino-[2',1':6,1]pyrido[3,4-b]indole-1,4-dione, 4-ethoxy-2-phenylcycloheptylimidazole, (6-bromo-3-methoxymethylimidazo[1,2-a]pyrazin-8-yl)methylamine, 8-[(phenylmethyl)thio]-4-(1-morpholinyl)-2-(1-piperazinyl)pyrimidino[4,5-d]pyrimidine, (+)-cis-5-methyl-2-[4-(trifluoromethyl)benzyl]-3,4,5,6a,7,8,9-octahydrocyclopent[4,5]imidazo[2,1-b]purin-4-one, cis-2-hexyl-5-methyl-3,4,5,6a,7,8,9,9a-octahydrocyclopent[4,5]imidazo[2,1-b]purin-4-one, 5[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), 1-[[3-(6,7-dihydro-1-methyl-7-oxo-3-propyl-1H-pyrazolo[4,3-d]pyrimidin-5-yl)-4-ethoxyphenyl]sulfonyl]-4-methylpiperazine, 2-(2-propoxyphenyl)purin-6(1H)-one, 2-(2-propoxyphenyl)-1,7-dihydro-5H-purin-6-one, methyl 2-(2-methylpyridin-4-ylmethyl)-1-oxo-8-(2-pyrimidinylmethoxy)-4-(3,4,5-trimethoxyphenyl)-1,2-dihydro-[2,7]naphthyridin-3-carboxylate, methyl 2-(4-aminophenyl)-1-oxo-7-(2-pyridinylmethoxy)-4-(3,4,5-trimethoxyphenyl)-1,2-dihydroisoquinoline-3-carboxylate, 2-[2-ethoxy-5-(4-ethylpiperazin-1-ylsulfonyl)phenyl]-5-methyl-7-propylimidazo[5,1-f][1,2,4]triazin-4(3H)-one (vardenafil), 3,4-dihydro-6-[4-(3,4-dimethoxybenzoyl)-1-piperazinyl]-2(1H)-quinolinone (vesnarinone), 1-cyclopentyl-3-methyl-6-(4-pyridyl)pyrazolo[3,4-d]pyrimidin-4(5H)-one, 1-cyclopentyl-6-(3-ethoxy-4-pyridinyl)-3-ethyl-1,7-dihydro-4H-pyrazolo[3,4-d]-pyrimidin-4-one, 6-o-propoxyphenyl-8-azapurin-6-one, 3,6-dihydro-5-(o-propoxyphenyl)-7H-v-triazolo[4,5-d]pyrimidin-7-one, 4-methyl-5-(4-pyridinyl)thiazole-2-carboxamide, 5-[2-ethoxy-5-(4-methylpiperazin-1-ylsulfonyl)phenyl]-1,6-dihydro-1-methyl-3-propylpyrazolo[4,3-d]pyrimidin-7-one, 5-[5-[(3S,5R)-3,5-dimethylpiperazin-1-yl]sulfonyl-2-ethoxyphenyl]-1-methyl-3-propyl-4H-pyrazolo[4,3-d]pyrimidin-7-one, 5-[5-[(3S,5R)-3,5-dimethylpiperazin-1-yl]sulfonyl-2-ethoxyphenyl]-1-methyl-3-propyl-4H-pyrazolo[4,3-d]pyrimidin-7-one, (6R,12aR)-6-(1,3-Benzodioxol-5-yl)-2-methyl-2,3,6,7,12,12a-hexahydropyrazino[1',2':1,6]pyrido[3,4-b]indole-1,4-dione, 2-[2-ethoxy-5-(4-ethylpiperazin-1-yl)sulfonylphenyl]-5-methyl-7-propyl-1H-imidazo[5,1-f][1,2,4]triazin-4-one, 3-(1-methyl-7-oxo-3-propyl-4H-pyrazolo[4,3-d]pyrimidin-5-yl)-N-[2-(1-methylpyrrolidin-2-yl)ethyl]-4-propoxybenzenesulfonamide, 4-[(3-chloro-4-methoxyphenyl)methylamino]-2-[(2S)-2-(hydroxymethyl)pyrrolidin-1-yl]-N-(pyrimidin-2-ylmethyl)pyrimidine-5-carboxamide, bis[2-[4-[4-ethoxy-3-(1-methyl-7-oxo-3-propyl-4H-pyrazolo[4,3-d]pyrimidin-5-yl)phenyl]sulfonyl-piperazin-1-yl]ethyl]carbonate, 5-ethyl-2-[5-[4-(2-hydroxyethyl)piperazin-1-yl]sulfonyl-2-propoxyphenyl]-7-propyl-1H-pyrrolo[3,2-d]pyrimidin-4-one, 2-[[2-[bis(2-hydroxyethyl)amino]-4,8-di(piperidin-1-yl)pyrimido[5,4-d]pyrimidin-6-yl]-(2-hydroxyethyl)amino]ethanol, 3-[(6-Deoxy-α-L-mannopyranosyl)oxy]-5-hydroxy-2-(4-methoxyphenyl)-8-(3-methyl-2-buten-1-yl)-4-oxo-4H-chromen-7-yl β-D-glucopyranoside, and 5-(2-propoxyphenyl)-2,3-dihydrotriazolo[4,5-d]pyrimidin-7-one and the pharmaceutically acceptable derivatives of these compounds. Many of these compounds and/or their pharmaceutically acceptable derivatives can also inhibit PDE6 and PDE9, As used herein, unless otherwise stated, a "pharmaceutically acceptable derivative" of an active compound means a pharmaceutically acceptable salt or solvate (e.g. hydrate), a pharmaceutically acceptable solvate of such salt, a pharmaceutically acceptable prodrug, a pharmaceutically acceptable N-oxide or a pharmaceutically acceptable salt or solvate of the latter.

"Pharmaceutically acceptable salts" refers to water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 1-hydroxy-2-naphthoic acid, the acids being employed in salt preparation—depending on whether it is a mono- or polybasic acid and depending on which salt is desired—in an equimolar quantitative ratio or one differing there from. Furthermore, the active compounds mentioned can also be present as pure enantiomers or as enantiomer mixtures in any mixing ratio.

"Pharmaceutically acceptable salts" also refers to salts with bases, e.g. alkali metal (lithium, sodium, potassium) or calcium, aluminum, magnesium, titanium, ammonium, meglumine or guanidinium salts, which also employ bases in salt preparations in an equimolar quantitative ratio or deviations of it.

"Pharmaceutically acceptable prodrugs" refers to a pharmacologically inactive form of one of the compounds described herein, which is then converted to an active form through metabolic processes such as hydrolysis of an ester. Prodrugs may improve bioavailability, resulting in tissue-specific delivery (e.g., to the kidney). An example of a PDE inhibitor prodrug is lodenafil carbonate, which is a carbonate ester dimer of lodenafil. Pharmaceutically inactive lodenafil carbonate is metabolized to the active lodenafil.

Active metabolites of any one of the phosphodiesterase inhibitors described herein are also contemplated herein. For example, UK-103,320 (N-Desmethyl sildenafil; 1-[4-ethoxy-3-(6,7-dihydro-1-methyl-7-oxo-3-propyl-1H-pyrazolo[4,3-d]pyrimidin-5-yl)phenyl-sulphonylpiperazine) is an active metabolite of sildenafil, inhibiting PDE5 with approximately 50% of the potency of the parent drug. M1 is an active metabolite of vardenafil capable of inhibiting PDE5, although with reduced potency. Active metabolites of other phosphodiesterase inhibitors described herein are known in the art. Active metabolites can be used in methods described herein on their own, in combination with their parent drug, in combination with other active metabolites, or in any other combination.

PDE6 Inhibitors

PDE6 subtypes are found in retinal rod and cone cells, where they tightly control cGMP hydrolysis. Many PDE5 inhibitors also significantly inhibit PDE6 (Zhang et al., *Invest. Ophthamol. Vis. Sci.*, (2005) 46.9, 3060.). Vardenafil was shown to be a potent PDE6 inhibitor, while Zaprinast was the only drug to inhibit PDE6 more potently than PDE5 (Zhang et el. (2005)).

PDE9 Inhibitors

As with PDE6, many PDE5 inhibitors also inhibit PDE9. There are relatively few PDE9-specific inhibitors, the first—BAY 73-6691 (1-(2-chlorophenyl)-6-[(2R)-3,3,3-trifluoro-2-methylpropyl]-1,5-dihydro-4H-pyrazolo[3,4-d]pyrimidine-4-one)—being reported in 2005 (Wunder et al., *Mol. Pharmacol.*, (2005) 68(6), 1775). BAY 73-6691 was developed by Bayer for treating Alzheimer's disease, and was shown to selectively inhibit human and murine PDE9 activity in vitro, and showed only moderate activity against other PDEs. The drug has not yet been approved by the FDA, but has been used in many cognition enhancement studies.

A second selective PDE9 inhibitor, also developed for improving cognitive dysfunction in Alzheimer's disease—PF-04447943 ((6-[(3S,4S)-4-methyl-1-(pyrimidin-2-ylmethyl)pyrrolidin-3-yl]-1-(tetrahydro-2H-pyran-4-yl)-1,5-dihydro-4H-pyrazolo[3,4-d]pyrimidin-4-one))—has been reported by Pfizer (Hutson et al., *Neuropharmacology*, (2011) 61(4), 665). PF-04447943 has been shown to be a potent, selective PDE9 inhibitor that elevates cGMP in brain and cerebrospinal fluid, enhances synaptic plasticity and improves memory in preclinical cognition models, and prevents decreases in dendritic spine density in amyloid precursor protein overexpressing transgenic mice.

Pharmaceutically acceptable derivatives of PF-04447943 and BAY 73-6691 may also be used in the methods and medicaments described herein.

In certain embodiments, PDE inhibitors useful in a method or medicament described herein include compounds selected from the group of sildenafil, aildenafil, tadalafil, vardenafil, udenafil, avanafil, lodenafil, mirodenafil, dipyridamole, icariin, zaprinast, PF-04447943, BAY 73-6691, and derivates, solvates, polymorphs, prodrugs, and/or the pharmacologically acceptable salts thereof.

Methods for Preventing Progression of and/or Treating Cystic Kidney Disease

Described herein is the discovery that inhibitors of PDE5, PDE6, and PDE9 are useful in reducing renal cyst size and preventing renal cyst growth. Methods for preventing the progression of and/or treating a cystic kidney disease in a subject in need thereof are described. The methods generally comprise administering an effective amount of at least one phosphodiesterase inhibitor capable of inhibiting at least one of PDE5, PDE6, and PDE9 to a subject.

As used herein, "preventing progression of" refers to slowing or halting the growth of renal cysts in a cystic kidney disease. Any slowed growth of renal cysts as compared to untreated renal cysts is considered to be a prevention of progression. Any stoppage of growth of renal cysts is also to be considered a prevention of progression.

"Treating" as it relates to cystic kidney disease refers to any reduction in size of a renal cyst in a subject having cystic kidney disease.

As used herein, "effective amount" refers to an amount of a substance, compound, or composition sufficient to prevent the progression of and/or treat a cystic kidney disease in a subject. An effective amount, or effective dose, can be administered in one or more administrations. The precise determination of an effective amount will be affected by factors individual to each subject, including but not limited to the subject's age, size, type and extent of disease, method of administration, whether the substance, compound, or composition is administered alongside conventional therapy (e.g. dialysis) or on its own, and the desired result. It will be known to one of skill in the art how to determine an effective amount for a particular subject.

The term "subject" as used herein may refer to any animal known to suffer from cystic kidney disease, including but not limited to human, feline, canine, equine, cattle, swine, sheep, and goat. In a particular embodiment, the subject is a human.

PDE inhibitors useful in methods described herein include, but are not limited to, compounds selected from the group of sildenafil (5-[2-ethoxy-5-(4-methylpiperazin-1-ylsulfonyl)phenyl]-1,6-dihydro-1-methyl-3-propylpyrazolo[4,3-d]pyrimidin-7-one, 5-[5-[(3S,5R)-3,5-dimethylpiperazin-1-yl]sulfonyl-2-ethoxyphenyl]-1-methyl-3-propyl-4H-pyrazolo[4,3-d]pyrimidin-7-one), aildenafil (5-[5-[(3S,5R)-3,5-dimethylpiperazin-1-yl]sulfonyl-2-ethoxyphenyl]-1-methyl-3-propyl-4H-pyrazolo[4,3-d]pyrimidin-7-one), tadalafil ((6R,12aR)-6-(1,3-Benzodioxol-5-yl)-2-methyl-2,3,6,7,12,12a-hexahydropyrazino[1',2':1,6]pyrido[3,4-b]indole-1,4-dione), vardenafil (2-[2-ethoxy-5-(4-ethylpiperazin-1-yl)sulfonylphenyl]-5-methyl-7-propyl-1H-imidazo[5,1-f][1,2,4]triazin-4-one), udenafil (3-(1-methyl-7-oxo-3-propyl-4H-pyrazolo[4,3-d]pyrimidin-5-yl)-N-[2-(1-methylpyrrolidin-2-yl)ethyl]-4-propoxybenzenesulfonamide), avanafil (4-[(3-chloro-4-methoxyphenyl)methylamino]-2-[(2S)-2-(hydroxymethyl)pyrrolidin-1-yl]-N-(pyrimidin-2-ylmethyl)pyrimidine-5-carboxamide), lodenafil (bis[2-[4-[4-ethoxy-3-(1-methyl-7-oxo-3-propyl-4H-pyrazolo[4,3-d]pyrimidin-5-yl)phenyl]sulfonylpiperazin-1-yl]ethyl]carbonate), mirodenafil (5-ethyl-2-[5-[4-(2-hydroxyethyl)piperazin-1-yl]sulfonyl-2-propoxyphenyl]-7-propyl-1H-pyrrolo[3,2-d]pyrimidin-4-one), dipyridamole (2-[[2-[bis(2-hydroxyethyl)amino]-4,8-di(piperidin-1-yl)pyrimido[5,4-d]pyrimidin-6-yl]-(2-hydroxyethyl)amino]ethanol), icariin (3-[(6-Deoxy-α-L-mannopyranosyl)oxy]-5-hydroxy-2-(4-methoxyphenyl)-8-(3-methyl-2-buten-1-yl)-4-oxo-4H-chromen-7-yl β-D-glucopyranoside), zaprinast (5-(2-propoxyphenyl)-2,3-dihydrotriazolo[4,5-d]pyrimidin-7-one), PF-04447943, BAY 73-6691, and derivates, solvates, polymorphs, prodrugs, active metabolites, and/or the pharmacologically acceptable salts of these compounds.

In a particular embodiment, the PDE inhibitor is sildenafil, or a pharmaceutically acceptable derivative thereof. In another embodiment, the PDE5 inhibitor is sildenafil citrate ([1-[[3-(6,7-dihydro-1-methyl-7-oxo-3-propyl-1H-pyrazolo[4,3-d]pyrimidin-5-yl)-4-ethoxyphenyl]sulfonyl]-4-methylpiperazine citrate).

In yet another embodiment, the PDE inhibitor is tadalafil, or a pharmaceutically acceptable derivative thereof.

In yet another embodiment, the PDE inhibitor is vardenafil, or a pharmaceutically acceptable derivative thereof. Examples of pharmaceutically acceptable salts of vardenafil include vardenafil hydrochloride, the trihydrate of vardenafil hydrochloride, and vardenafil dihydrochloride.

In certain embodiments, the cystic kidney disease to be treated and/or progression thereof slowed is a polycystic disease such as autosomal dominant polycystic kidney disease and autosomal recessive polycystic kidney disease. In a particular embodiment, the cystic kidney disease is autosomal dominant polycystic kidney disease.

Medicaments for Preventing Progression of and/or Treating Cystic Kidney Disease

Medicaments, or pharmaceutical preparations, for preventing progression of and/or treating cystic kidney disease are described herein. In particular, pharmaceutical preparations described herein can be used to prevent progression of and/or treat polycystic kidney diseases. In an embodiment, the medicament can be used to prevent progression of and/or treat autosomal dominant polycystic kidney disease.

As a medicament, one or more PDE inhibitors described herein are employed as such, or, in certain embodiments, are in combination with suitable pharmaceutical carriers, vehicles, or excipients comprising inert ingredients. A medicament or pharmaceutical preparation also refers to any product that results, directly or indirectly, from combination, complexation, or aggregation of any two or more of the ingredients, or from dissociation of one or more of the ingredients, or from other types of reactions or interactions of one or more of the ingredients. Generally, pharmaceutical preparations are prepared by uniformly and intimately bringing the active ingredient into association with a liquid carrier, vehicle, or excipient, or a finely divided solid carrier, vehicle, or excipient, or both, and then, if necessary, shaping the product into the desired formulation. The pharmaceutical preparation includes enough of the active ingredient to produce the desired effect. By "pharmaceutically acceptable" it is meant that the carrier, vehicle, or excipient must be compatible with the other ingredients of the formulation and not deleterious to the recipient thereof.

Compounded medicaments may be in the form of, for example, tablets, coated tablets, capsules, caplets, suppositories, films, emulsions, suspensions, gels, or solutions. In certain embodiments, a medicament described herein comprises a total amount of active compound in the range from about 0.05 to about 99% w (percent by weight, based on total preparation). In other embodiments, a medicament described herein comprises a total amount of active compound in the range from about 0.10 to about 70% w. In yet other embodiments, a medicament described herein comprises a total amount of active compound in the range from about 0.10 to about 50% w. By the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with carriers, vehicles, and excipients suitable for the desired pharmaceutical formulations on account of their expert knowledge. In addition to solvents, gel formers, ointment bases and other active compound excipients, for example antioxidants, dispersants, emulsifiers, preservatives, solubilizers, colorants, complexing agents, preservatives, flavors, buffering agents, viscosity-regulating agents, surfactants, adjuvants, binders, lubricants, carriers, diluents, stabilizers, or permeation promoters, can be used.

In particular embodiments, a medicament comprising one or more PDE inhibitors described herein further comprises a kidney-targeting drug delivery system. Such systems are known in the art, and may include but are not limited to: macromolecular carriers including lysozyme, low molecular weight chitosan, poly(vinylpyrrolidone-co-dimethyl maleic acid), and G3-C12 peptide; prodrugs including sugar-modified prodrugs, amino acid-modified prodrugs, and folate-modified prodrugs; nanoparticles; and liposomes. For a review of kidney-targeted drug delivery systems, please see Zhou et al., *Acta Pharmaceutica Sinica B*, (2014) 4(1), 37.

Tablet formulations for sildenafil, tadalafil, vardenafil, and avanafil are commercially available under the trade names Viagra®, Cialis®, Levitra®, and Stendra®, respectively.

The amount of PDE5 inhibitor, or a pharmaceutical acceptable derivative thereof, which is required to achieve a therapeutic effect will, of course, vary with the particular compound, the route of administration, the subject under treatment, and the particular disorder or disease being treated. As a monotherapy, a cGMP-specific PDE inhibitors are generally administered to adult humans by oral administration at a dose of 1 to 200 mg daily. As a monotherapy, sildenafil, vardenafil, tadalafil, and avanafil are generally administered to adult humans by oral administration at a dose of 1 to 200 mg daily.

Commercially available tablet formulations for sildenafil contain 25, 50 or 100 mg of sildenafil. Commercially available tablet formulations for vardenafil contain 5, 10 or 20 mg of vardenafil. Commercially available tablet formulations for tadalafil contain 10 or 20 mg of tadalafil. Commercially available tablet formulations for avanafil contain 100 or 200 mg of avanafil.

Method of Diagnosing Cystic Kidney Disease

As described herein, PDE5, PDE6, and PDE9 were significantly upregulated in all cystic kidney tissues examined. In another embodiment described herein is a method for diagnosing a cystic kidney disease in a subject. Generally, the method comprises providing a renal cell and/or tissue sample from the subject, determining the levels of PDE5, PDE6, and PDE9 gene expression in the renal cell and/or tissue sample, and diagnosing cystic kidney disease in the subject when the determined levels of PDE5, PDE6, and PDE9 gene expression are higher than those found in cell and/or tissue sample from a population of healthy subjects.

In some embodiments of the present methods, use of a control is desirable. In that regard, the control may be a cell/tissue sample obtained from at least one healthy subject, such as a healthy subject not suffering from cystic kidney disease. In another example, the control is a standard calculated from historical values. In certain embodiments, the population of healthy subjects comprises an individual subject, at least 5 individual subjects, at least 10 individual subjects, at least 20 individual subjects, at least 50 individual subjects, or at least 100 individual subjects.

Renal cell and/or tissue samples can be collected by any means known in the art, including but not limited to percutaneous biopsy (renal needle biopsy), and open biopsy. Percutaneous biopsy may be guided by ultrasound or computed tomography (CT) scan to direct the needle to a specific area of the kidney.

The level of at least one cGMP-related PDE gene product can be measured in cells of a biological sample obtained from the subject. For example, a tissue sample can be removed from a subject suspected of having cystic kidney disease, by conventional biopsy techniques. In one embodiment, the tissue sample is obtained from the subject prior to therapeutic treatment. A corresponding control tissue sample, or a control reference sample, can be obtained from a healthy human individual or population of healthy individuals free from cystic kidney disease. The control tissue sample is then processed along with the sample from the subject, so that the levels of cGMP-related PDE gene product produced from a given PDE gene in cells from the subject's sample can be compared to the corresponding PDE gene product levels from cells of the control sample. Alternatively, a reference sample can be obtained and processed separately (e.g., at a different time) from the test sample and the level of a PDE gene product produced from a given PDE gene in cells from the test sample can be compared to the corresponding PDE gene product level from the reference sample.

In one embodiment, the level of the at least one cGMP-related PDE gene product in the test sample is greater than the level of the corresponding PDE gene product in the control sample (i.e., expression of the PDE gene product is "up-regulated" or "increased"). The relative PDE gene expression in the control and normal samples can be determined with respect to one or more RNA expression standards. The standards can comprise, for example, a zero PDE gene expression level, the PDE gene expression level in a standard cell line, or the average level of PDE gene expression previously determined in a population of healthy controls.

An increase in the level of a PDE gene product in the sample obtained from the subject, relative to the level of a corresponding PDE gene product in a control sample, is indicative of cystic kidney disease. In a certain embodiment, the at least one PDE gene product is a gene product of PDE5, PDE6, or PDE9. In certain embodiments, a diagnosis of cystic kidney disease is made when the gene expression levels of PDE5, PDE6, and PDE9 are significantly higher than those in the population of healthy subjects, as determined by any statistical method known in the art (e.g., t-test). Significance is determined where p<0.05.

The level of a PDE gene product in a sample can be measured using any technique that is suitable for detecting RNA expression levels in a biological sample. Suitable techniques (e.g., Northern blot analysis, quantitative RT-PCR, in situ hybridization) for determining RNA expression levels in a biological sample (e.g., cells, tissues) are well known to those of skill in the art. In a particular embodiment, the level of at least one PDE gene product is detected using Northern blot analysis. In another embodiment, the level of at least one PDF gene product is detected using quantitative RT-PCR analysis. In yet another embodiment, the level of at least one PDE gene product is detected using in-situ hybridization analysis.

In one embodiment, the invention provides methods of diagnosing whether a subject has cystic kidney disease, comprising reverse transcribing RNA from a test sample obtained from the subject to provide a set of target oligodeoxynucleotides, hybridizing the target oligodeoxynucleotides to a microarray comprising PDE-specific probe oligonucleotides to provide a hybridization profile for the test sample, and comparing the test sample hybridization profile to a hybridization profile generated from a control sample, wherein an increase in the signal of at least one PDE gene product is indicative of the subject having cystic kidney disease. In a particular embodiment, the microarray comprises PDE-specific probe oligonucleotides for human PDEs.

The microarray can be prepared from gene-specific oligonucleotide probes generated from known PDE sequences. The array may also contain controls, such as one or more mouse sequences differing from human orthologs by only a few bases, which can serve as controls for hybridization stringency conditions. tRNAs and other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known PDE nucleic acid sequences. The microarray may be fabricated using techniques known in the art.

In certain embodiments the diagnostic methods described herein can be used to diagnose a polycystic kidney disease such as autosomal dominant polycystic kidney disease or autosomal recessive polycystic kidney disease. In a one embodiment, the diagnostic methods described herein can be used to diagnose autosomal dominant polycystic kidney disease.

EXAMPLES

The methods and embodiments described herein are further defined in the following Examples. Certain embodiments of the present invention are defined in the Examples herein. It should be understood that these Examples, while indicating preferred embodiments of the invention, are given by way of illustration only. From the discussion herein and these Examples, one skilled in the art can ascertain the essential characteristics of this invention and without departing from the spirit and scope thereof, can make various changes and modifications of the invention to adapt it to various usages and conditions.

Example 1. Transcriptogram Analysis Showing Upregulation of PDE5, PDE6, and PDE9 in Cystic Kidney Disease Overview Transcriptogram analysis, developed by the de Almeida lab, is a method for whole genome gene expression data analysis that more sensitively identifies affected molecular networks and pathways (Rybarczyk-Filho et al. (*Nucleic Acids Res.*, 39(8): 3005-15 (2011)) than conventional methods. Genes are ordered into a list using a Monte Carlo Simulation that minimizes distance between associated gene products, such that proximity on the list correlates with co-participation in biological processes. Transcriptogram profiles are then produced by calculating the average transcription level for genes within a moving window. The resulting transcriptogram reveals which pathways are differentially expressed. This approach provides a robust statistical approach that couples enhanced significance discovery with assessment of false discovery rate.

ADPKD Cell Lines

Human renal epithelial cells were isolated from normal human kidneys (deemed unusable for transplant) and age/sex matched human ADPKD kidney.

Epithelial cells isolated from ADPKD kidneys were micro-dissected from cysts and grown in culture. In one early ADPKD kidney, cysts and non-cystic tubules were dissected out. All cell lines were grown in primary culture for 4 passages then immortalized with a retrovirus carrying hTERT (human telomerase). A G418 selection gene was also carried on the retrovirus. All immortalized cells were grown on membrane filter supports and RNA was isolated using Trizol Reagent.

200 ng of purified total RNA was labeled using the Agilent QuickAmp labeling kit, 1-color (Agilent Technologies, Palo Alto, Calif.). Hybridization of purified cRNA was performed to a custom Agilent Human Whole Genome 4×180K array which contains the content of the v2 4×44 k array replicated at least 4 times (AMIDID 026822). After hybridization at 65° C., 20 rpm for 17 hours, arrays were washed in wash buffer 1 (6×SSC, 0.005% TritonX-102) for five minutes at room temperature and wash buffer 2 (0.06× SSC, 0.005% Triton X-102) for five minutes at 37° C. Arrays were scanned on the Agilent High-Resolution Microarray B-series Scanner (G2505B). Data was extracted from images using the Agilent Feature Extraction software (version 10.7).

Transcriptogram Analysis

Ordering Process

Transcriptograms give an integrated visualization of genome wide gene expression data (Rybarczyk-Filho et al, 2011) by projecting expression levels on conveniently ordered gene list, to produce a genome wide expression profile. The gene list ordering is based on protein-protein association information retrieved from STRING database (Szkiarczyk et al., *Nucleic Acids Research*, 2011:D561-D568 (2011)) with confidence score of 0.800 and considering all methods to infer protein-protein associations, with exception to text mining. The ordering process is performed by a Monte Carlo algorithm that minimizes a cost function F chosen to approximate associated genes on the list, given as:

$$F = \sum_{i=1}^{N-1} \sum_{j=i+1}^{N} d_{ij}^a (|A_{ij} - A_{i+1,j}| + |A_{ij} - A_{i-1,j}| + |A_{ij} - A_{ij+1}| + |A_{ij} - A_{ij-1}|)$$ (equation 1)

where N is the number of genes on the list and Aij is the association matrix and is 1 when the products of the genes at positions i and j in the list are associated and 0 otherwise. di j=i−j measure how far the genes are located on the list. Minimizing F favors clusters of associated genes on the list. The minimization procedure starts with a randomly ordered gene list, with all and only genes whose products have at least one association. Then a pair of genes is randomly chosen, their positions are tentatively swapped and the change in the cost function F is calculated. The position swap is accepted whenever F=0 or, if F>0, the swap is accepted with probability exp−F/T. T is a temperature-like parameter that intended to allow the escape from eventual metastable states. The algorithm performs a simulated annealing (Bertsimas, D and Tsitsiklis J. *Statistical Science*, 8:10-15 (1993)) by starting from a high value for T and decreasing its value gradually every 100 Monte Carlo Step (MCS). One MCS equals to a N choices of gene pairs. To avoid metastable configurations of the list, the set of genes belonging to the olfactory perception pathway were artificially segregated: it consists of a large gene set with all genes associated to one another.

Pathways Profiles

This ordering procedures produces ordered gene list where the probability that any two genes are associated exponentially decays with their distance measured over the list. STRING database for protein-protein association has the KEGG pathways (Szkiarczyk et al., 2011; Kanehisa et al., *Nucleic Acids Research*, 38:D355-D360 (2010)) as the golden rule to attribute confidence scores, such that a high confidence means that the probability that the associated genes are listed in a same KEGG pathway are also high. The ordered list consequently group genes by the biological function. GO term or KEGG pathway profiles are obtained by first creating a vector of N dimensions and assigning 1 or 0 to each element i of the vector depending on whether the position i of the ordered list corresponds to a gene that participates or not in the GO term or KEGG pathway. Then an average is performed over a running window of size 2 r+1 and assigned to the central window position. The resulting profile peaks indicate the intervals on the list enriched with genes of the related GO term or KEGG pathway.

Transcriptogram Production

Microarray data is projected on the ordered list and, since neighboring genes are expected to have their products associated, the gene expression correlates with position. Average of gene expression is taken over a running window of 2r+1 genes and its value is assigned to the central gene position, in a process known as boxcar average. The resulting profile is the transcriptogram for that expression data, and may be plotted as a function of gene position.

Class Comparison

Comparisons are made relatively to one class, chosen as control. First, normal and then non-cystic ADPKD samples were considered as controls. In a transcriptogram comparison, first the transcriptograms are produced, here taking r=30 (the running window size of 61). Then all transcriptogram values are averaged over the samples of each class, producing a class average transcriptogram profile and the corresponding standard error. Finally, the class averages for each gene location i, (i=1, . . . , N), is divided by the corresponding value of the control class, producing a relative average transcriptogram.

Significance Evaluation

When comparing two classes, significance is estimated in two different complementary ways. First a P-value is obtained, by comparing the class averages for the transcriptograms for each ordering position i, using a two tail Welch's t-test. Second, a false discovery rate (FDR) is estimating by permuting the sample labels (phenotypes). 500 permutations were considered. Biological interpretation: Projection of KEGG pathways and GOBP terms Biological interpretations is facilitated by comparing the enrichment with GOBP terms and KEGG pathways at the regions of the ordered indicates as significantly altered between the compared classes. Here, David Annotation Tools (Huang, et al., 2009) was used. For each pathway or term, a profile was obtained (as described above) for r=30.

Results

Gene Ordering in Transcriptome Analysis

Figure 6:
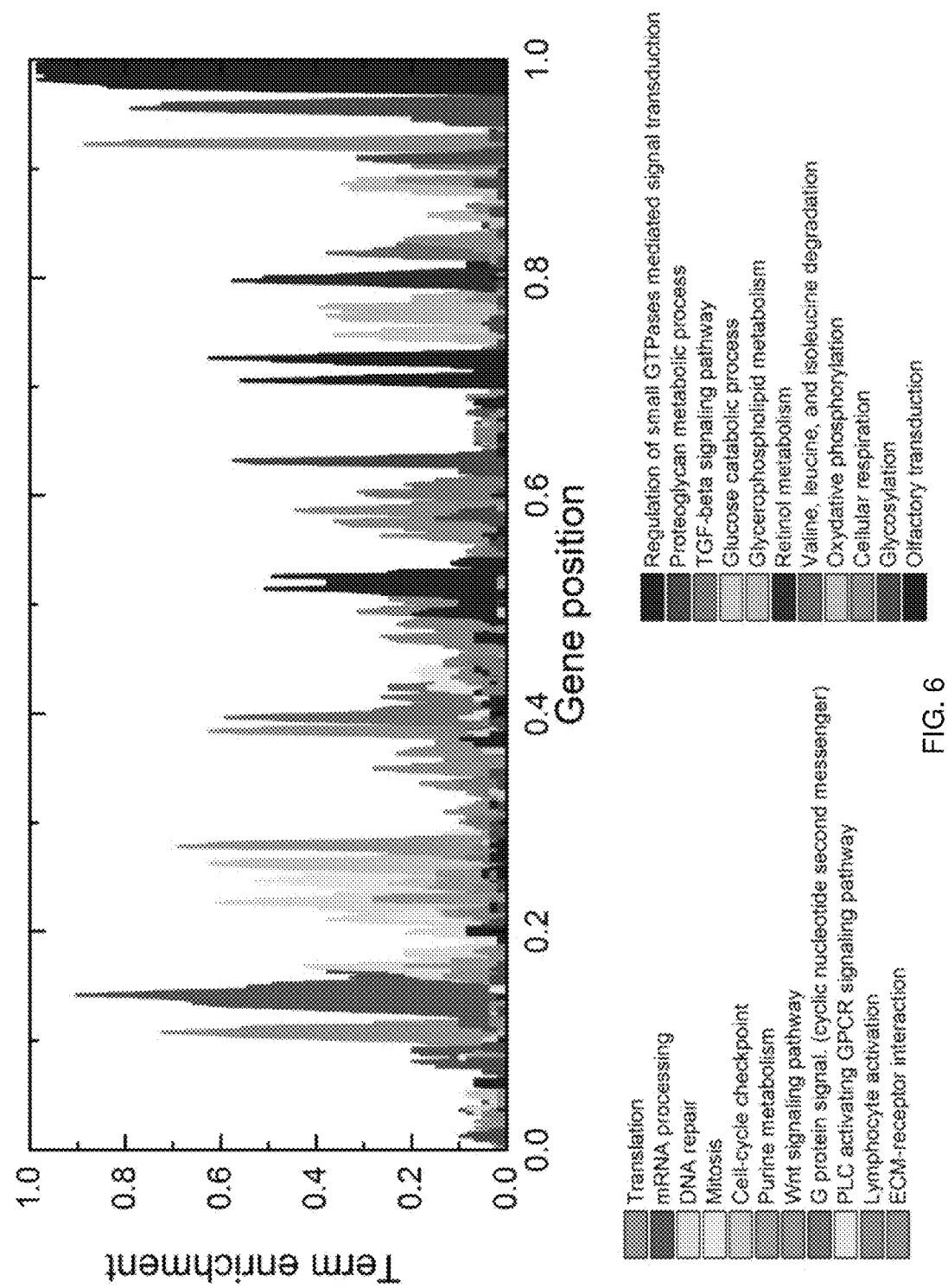
FIG. 6: Transcriptogram analysis showing gene ordering. The abscissa axis stands for the ordered gene list, comprising 9684 genes. The colored profiles give the density distributions of the GOBP terms or KEGG pathways, as indicated in the legend. High peaks mean that at that point the list is enriched with genes of the term or pathway.

FIG. 6. depicts the biological logic of the ordered gene list. The abscissa axis stands for the ordered gene list, comprising 9684 genes. The colored profiles give the density distributions of the GOBP terms or KEGG pathways, as indicated in the legend. High peaks mean that at that point the list is enriched with genes of the term or pathway.

Direct Transcriptogram Comparison: Non-Cystic ADPKD Vs. Normal Cells

Figure 7:
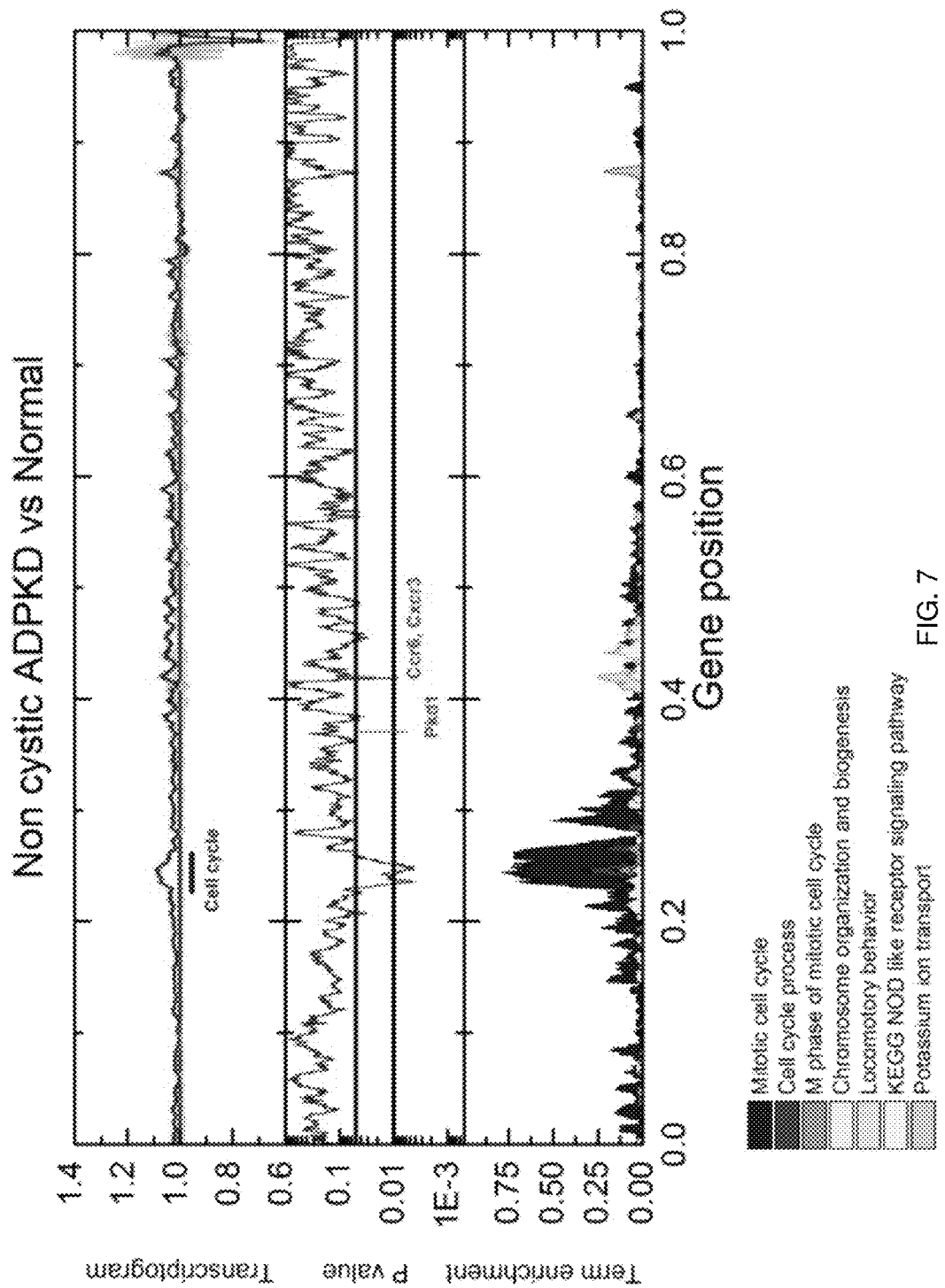
FIG. 7: Direct transcriptogram comparison of non-cystic ADPKD vs. normal cells. The upper panel shows relative average transcriptograms for Non-cystic (dark blue) and Normal (light blue), relative to Normal. Shaded areas represent standard error. The central panel presents the P-value from a two tail Weyl's t-test for each point along the transcriptogram, with horizontal lines marking $P=0.05$ and $P=0.01$. The lower panel projects onto the ordered list some of the GOBP terms and KEGG pathways that are differentially expressed. The transcriptograms mostly overlap with exceptions marked by inverted peaks in the P-values. Note the cell cycle region of the ordered list that corresponds with overexpression in non-cystic ADPKD samples and P values <0.01.

FIG. 7 shows the transcriptogram analysis for Non-cystic ADPKD vs. Normal samples. The abscissa axis represents the ordered gene list. The upper panel shows relative average transcriptograms for Non cystic (blue) and Normal (black), relative to Normal. Shaded areas represent standard error. The central panel presents the P-value from a two tail Weyl's t-test for each point along the transcriptogram, with horizontal lines marking P=0.05 and P=0.01. The lower panel projects onto the ordered list some of the GOBP terms and KEGG pathways that are differentially expressed. The transcriptograms mostly overlap with exceptions marked by inverted peaks in the P-values. Note the cell cycle region of the ordered list that corresponds with overexpression in non-cystic ADPKD samples and P values <0.01.

Direct Transcriptogram Comparison: Cystic ADPKD Vs. Normal Cells

Figure 8:
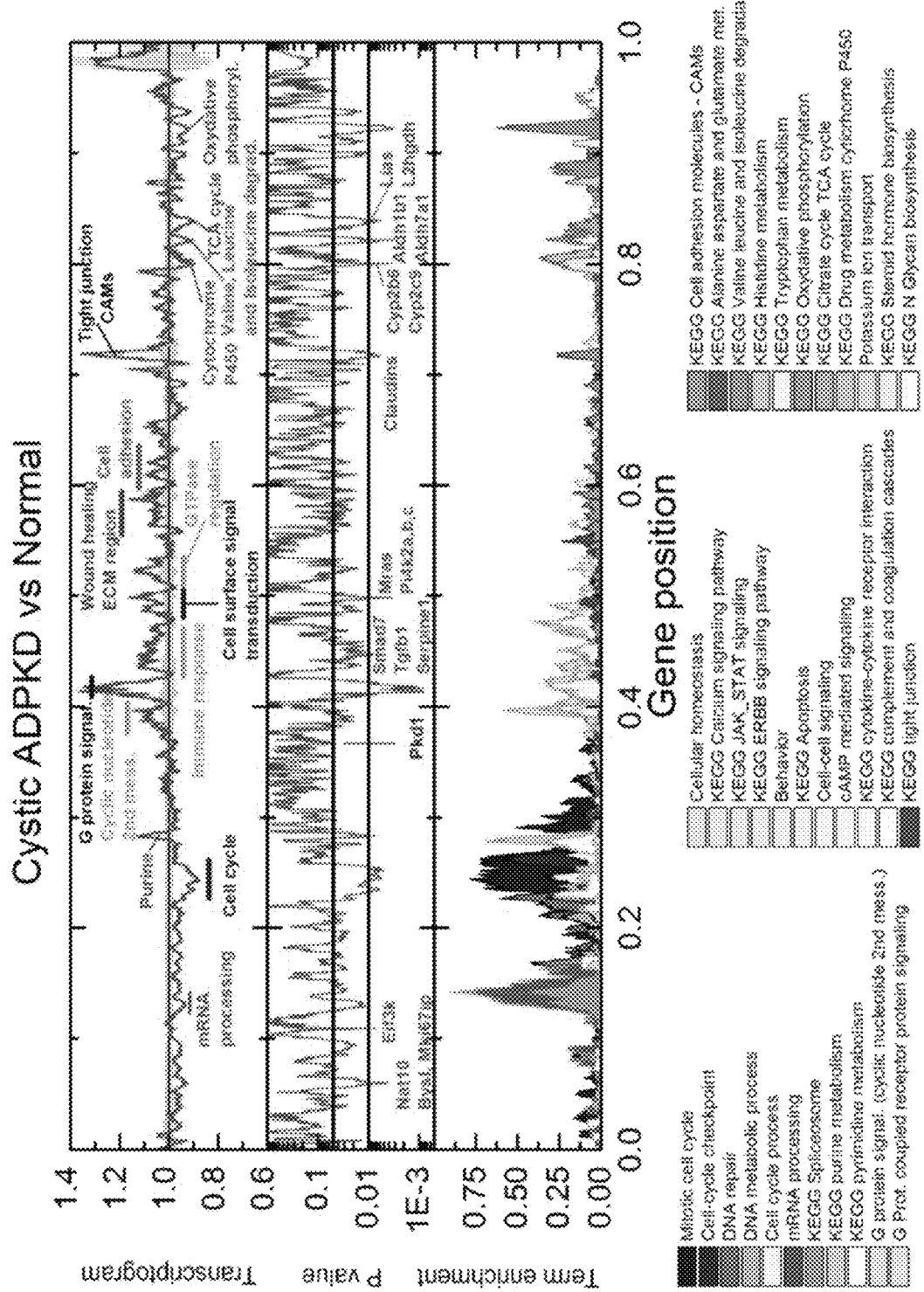
FIG. 8: Direct transcriptogram comparison of cystic ADPKD vs. normal cells. The transcriptogram shows many regions of the ordered list with significant differential expression, as represented by the profile peaks. The mitotic cell cycle region of the ordered list shows down regulation in Cystic samples, with P values <0.01 and enrichment peaks for related terms. Other significant differential expression occurs in regions enriched with genes associated with G protein signaling pathways, tight junctions, cell adhesion and energy metabolism.

FIG. 8 shows the transcriptogram of Cystic ADPKD cells vs. Normal. The transcriptogram shows many regions of the ordered list with significant differential expression. The mitotic cell cycle region of the ordered list shows down regulation in Cystic samples, with P values <0.01 and enrichment peaks for related terms. Other significant differential expression occurs in regions enriched with genes associated with G protein signaling pathways, tight junctions, cell adhesion and energy metabolism.

Figure 9:
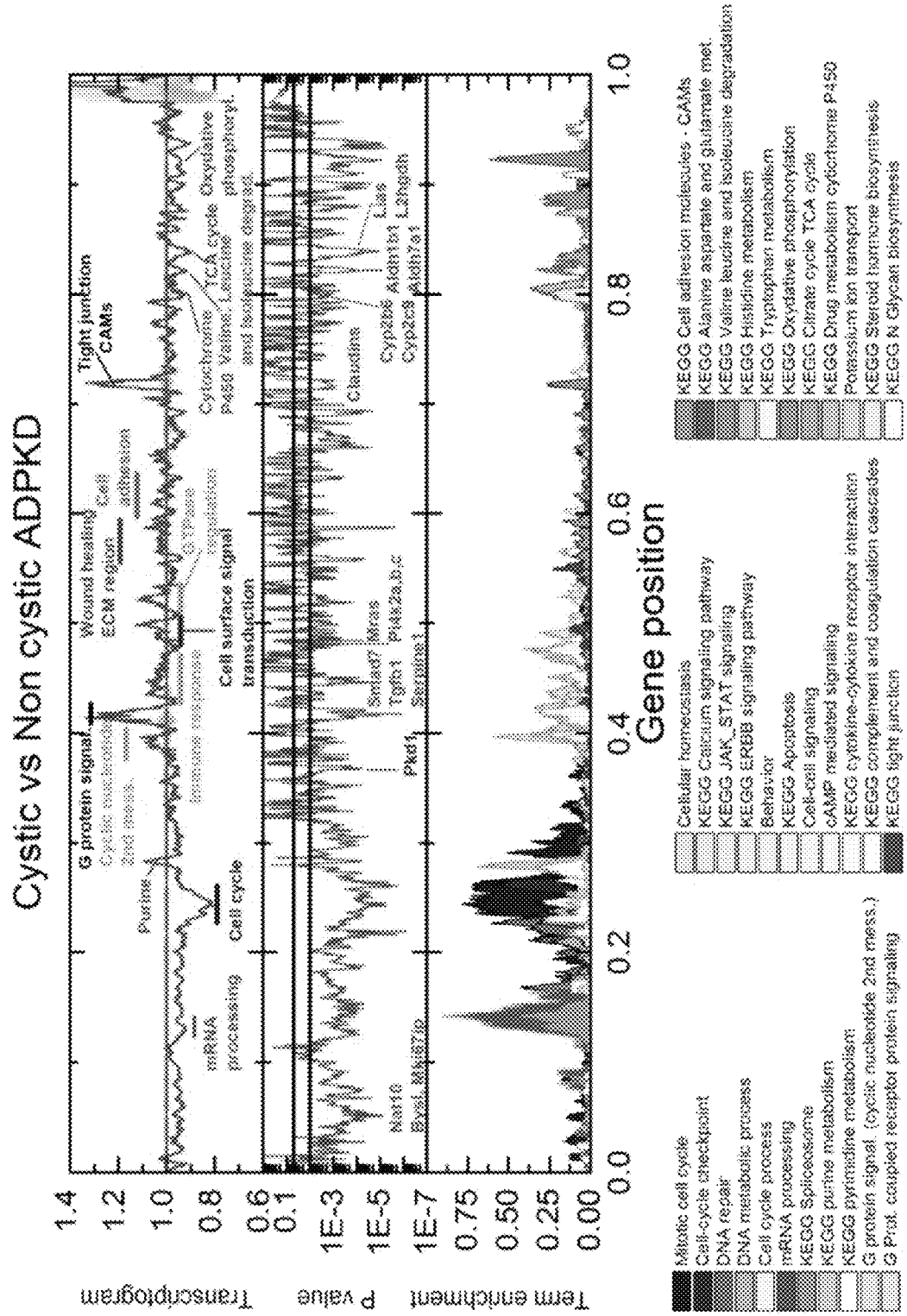
FIG. 9: Direct transcriptogram comparison of cystic ADPKD Vs. non-cystic ADPKD from the same kidney. The transcriptogram shows many regions of differential expression, as represented by the profile peaks. The overall trend is the same as the comparison of cystic ADPKD with Normal. The P-values are consistently lower than comparisons with Normal (FIGS. 4 and 5) because the standard errors in non-cystic ADPKD samples were consistently lower than that of Normal.

Direct Transcriptogram Comparison: Cystic ADPKD Vs. Non-Cystic ADPKD from the Same Kidney FIG. 9 shows the transcriptogram of non-cystic ADPKD vs. cystic ADPKD cells from the same kidney, showing multiple regions of differential expression. The overall trend is the same as the comparison of cystic ADPKD with Normal. The P-values are consistently lower than comparisons with Normal (FIGS. 4 and 5) because the standard errors in non-cystic ADPKD samples were consistently lower than that of Normals.

Figure 10:
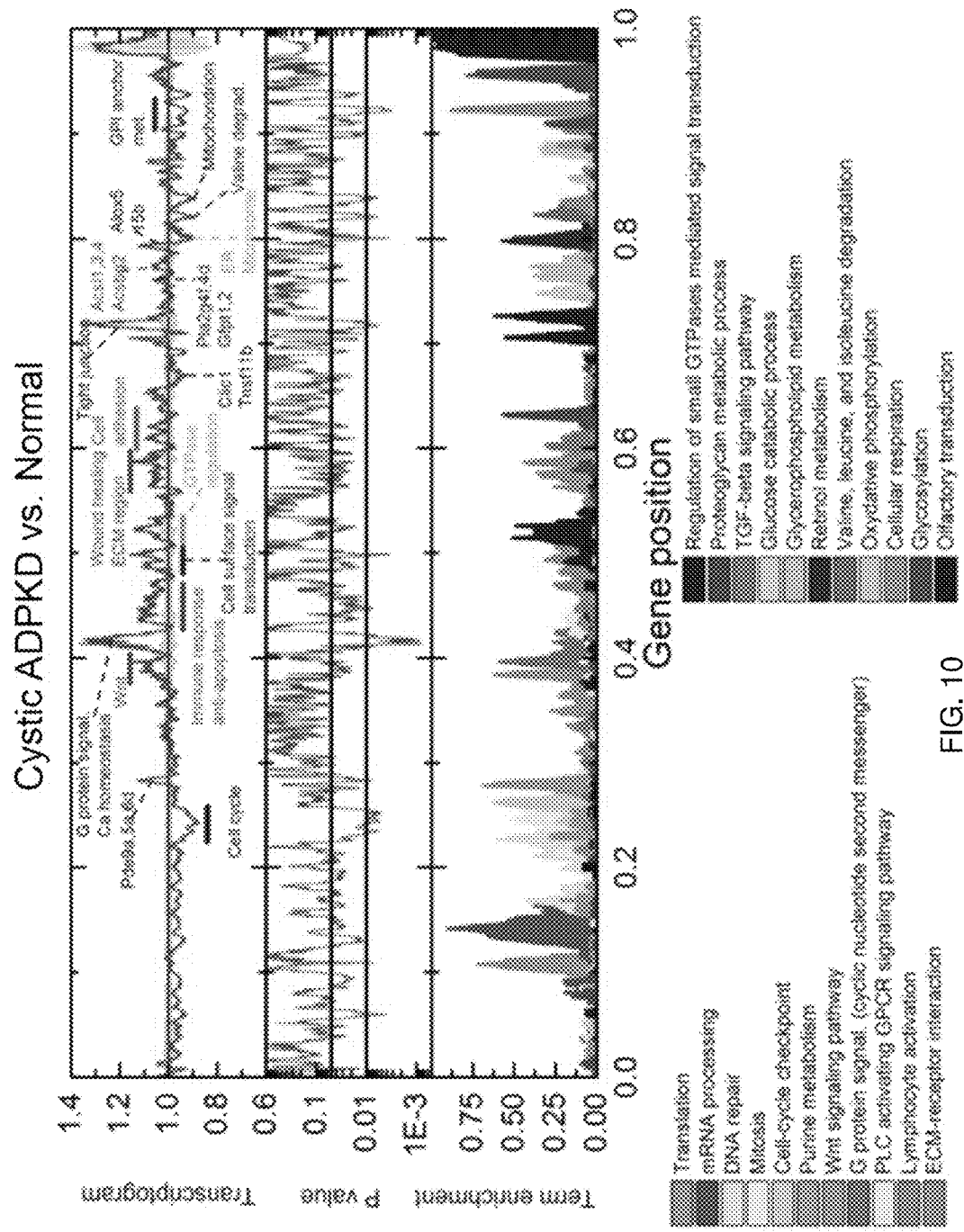
FIG. 10: Transcriptogram of cystic ADPKD Vs. normal shows purine metabolism peak, and increases in expression of cGMP phosphodiesterases PDE5, PDE6, and PDE9.

Transcriptogram of Cystic ADPKD Vs. Normal Shows Purine Metabolism Peak, cGMP Phosphodiesterases As shown in FIG. 10, transcriptogram analysis revealed enrichment in genes associated with purine metabolism and G protein signaling pathways, specifically, cGMP phosphodiesterases. PDE5, PDE6, and PDE9 were all found to be upregulated in every type of cystic kidney tissue examined. The upregulation of PDE5, PDE6, and PDE9 is shown in the upper transcriptogram panel of FIG. 10 as a labeled profile peak.

Example 2. Sildenafil Citrate Reduces Renal Cyst Size and Prevents Renal Cyst Growth In a kidney cell tubule culture system model for renal cyst formation, sildenafil citrate (sold under the trade name Viagra®) both reduced average cyst size, and prevented the growth of cysts.

Telomerase immortalized polycystic kidney cells, as described in Herbert et al. (*PLoS One* (2013), 8(1): e55191; which is hereby incorporated by reference in its entirety), were used to test the effect of sildenafil citrate on renal cyst growth. Cells from polycystic kidneys removed from patients for medically indicated reasons, removed from any research program, were obtained. The cells were obtained from the pathology laboratory. Cyst tissue was microdissected from the kidneys, and cells were isolated and grown in primary culture. The cells were then immortalized using retroviral techniques well known in the art. Following confirmation of an immortal phenotype, it was established that the polycystic cyst epithelial cells formed cyst structures when grown in 3D forskolin-supplemented Matrigel culture.

Immortalized polycystic kidney cells were treated with microgram dosages of sildenafil citrate of 4 µg/ml, 2 µg/ml, and 1 µg/ml. Average cyst size was significantly decreased compared to control (p<1 E−6 for 4 ug/ml dose, p<0.01 for 2 ug/ml dose, and p<0.01 for the 1 ug/ml dose).

As shown in FIG. 1, cells were also treated with 250, 500, or 1000 ng/ml sildenafil citrate. Matched controls were sham-treated with vehicle but no drug. Cyst area was quantified and average cyst area was found to be significantly reduced in sildenafil citrate-treated cultures (p<1.05 E−8 for 250 ng/ml dose, p<0.01 for 500 ng/ml dose, and p<0.01 for the 1000 ng/ml dose FIG. 1). No dose response was observed, showing that lower doses are similarly effective as higher doses. Dosages tested were consistent with the range of serum drug levels that occur when the drug is prescribed for erectile dysfunction. These results show that lower concentrations will be effective as well.

Depicted in FIG. 2, frequency distribution analysis showed that average cyst size was reduced by sildenafil citrate, as large cysts were absent from sildenafil citrate treated cultures. The depicted frequency distribution, which indicates the frequency of cysts of designated size, indicates that while large cyst structures of greater than $150\mu^2$ continued to form in vehicle-treated control cells, treatment with sildenafil citrate completely inhibited large cyst formation. These results demonstrate the ability of cGMP-specific PDE inhibitors to reduce average renal cyst size and prevent renal cyst growth. The complete absence of large cysts shows that sildenafil citrate slows the progression of polycystic kidney diseases, which is more beneficial than a simple small reduction in all sizes of cysts.

As shown in FIGS. 3A-5B, no large cysts were observed in cells treated with sildenafil. Cells were treated with a dilution of sildenafil in vehicle from a stock (FIGS. 3B (1:250), 4B (1:500), and 5B (1:1000)), or with control (no sildenafil; FIGS. 3A, 4A, and 5A). Images were collected with a 20× phase contrast objective.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiments disclosed herein contemplated for carrying out this invention, but that the invention will include all embodiments falling within the scope of the claims.

What is claimed is:

1. A method for preventing the progression of and/or treating a cystic kidney disease in a subject in need thereof, comprising administering an effective amount of at least one phosphodiesterase inhibitor, at least one pharmaceutically effective phosphodiesterase inhibitor prodrug, at least one pharmaceutically active phosphodiesterase inhibitor metabolite, or a combination thereof to the subject, wherein the phosphodiesterase inhibitor and the pharmaceutically active phosphodiesterase inhibitor metabolite individually inhibits at least one phosphodiesterase selected from the group consisting of: phosphodiesterase type 5; phosphodiesterase type 6; and phosphodiesterase type 9, and the pharmaceutically effective phosphodiesterase inhibitor prodrug is convertible to an active inhibitor of at least one phosphodiesterase selected from the group consisting of: phosphodiesterase type 5; phosphodiesterase type 6; and phosphodiesterase type 9.

2. A method for preventing the progression of and/or treating a cystic kidney disease in subject in need thereof, comprising administering an effective amount of at least one compound, wherein each of the at least one compounds is individually selected from the group consisting of: sildenafil; aildenafil; tadalafil; vardenafil; udenafil; avanafil; lodenafil; mirodenafil; dipyridamole; icariin; zaprinast; PF-04447943; BAY 73-6691; a pharmaceutically acceptable salt of sildenafil, aildenafil, tadalafil, vardenafil, udenafil, avanafil, lodenafil, mirodenafil, dipyridamole, icariin, zaprinast, PF-04447943, or BAY 73-6691; a hydrate of the pharmaceutically acceptable salt of sildenafil, aildenafil, tadalafil, vardenafil, udenafil, avanafil, lodenafil, mirodenafil, dipyridamole, icariin, zaprinast, PF-04447943, or BAY 73-6691; a pharmaceutically effective prodrug of sildenafil, aildenafil, tadalafil, vardenafil, udenafil, avanafil, lodenafil, mirodenafil, dipyridamole, icariin, zaprinast, PF-04447943, or BAY 73-6691; and a pharmaceutically active metabolite of sildenafil, aildenafil, tadalafil, vardenafil, udenafil, avanafil, lodenafil, mirodenafil, dipyridamole, icariin, zaprinast, PF-04447943, or BAY 73-6691.

3. The method of claim 1, wherein the at least one phosphodiesterase inhibitor is selected from the group consisting of: sildenafil; a pharmaceutically acceptable salt of sildenafil; and a pharmaceutically effective prodrug of sildenafil.

4. The method of claim 1, wherein the at least one phosphodiesterase inhibitor is sildenafil citrate.

5. The method of claim 1, wherein the at least one phosphodiesterase inhibitor is selected from the group consisting of: tadalafil; a pharmaceutically acceptable salt of tadalafil; and a pharmaceutically effective prodrug of tadalafil.

6. The method of claim 1, wherein the at least one phosphodiesterase inhibitor is selected from the group consisting of: vardenafil; a pharmaceutically acceptable salt of vardenafil; and a pharmaceutically effective prodrug of vardenafil.

7. The method of claim 1, wherein the at least one phosphodiesterase inhibitor is selected from the group consisting of: vardenafil hydrochloride; trihydrate of vardenafil hydrochloride; and vardenafil dihydrochloride.

8. The method of claim 1, wherein the cystic kidney disease is a polycystic kidney disease selected from the group consisting of: autosomal dominant polycystic kidney disease; and autosomal recessive polycystic kidney disease.

9. The method of claim 1, wherein the subject is an individual selected from the group consisting of: human; feline; canine; equine; cattle; swine; sheep; and goat.

10. The method of claim 1, wherein each of the at least one phosphodiesterase inhibitors is individually selected from the group consisting of: a pharmaceutically effective derivative of sildenafil; aildenafil; tadalafil; vardenafil; udenafil; avanafil; lodenafil; mirodenafil; dipyridamole; icariin; zaprinast, PF-04447943, BAY 73-6691, a pharmaceutically acceptable salt thereof; and a hydrate of the pharmaceutically acceptable salt thereof.

11. The method of claim 1, wherein the effective amount of the at least one phosphodiesterase inhibitor, at least one pharmaceutically effective phosphodiesterase inhibitor prodrug, at least one pharmaceutically active phosphodiesterase metabolite, or combination thereof is associated with a kidney-targeted drug delivery system.

12. The method of claim 11, wherein the kidney targeted drug delivery system is of a type selected from the group consisting of: lysozyme; low molecular weight chitosan; poly(vinylpyrrolidone-co-dimethyl maleic acid); G3-C12 peptide; sugar-modified prodrugs; amino acid-modified prodrugs; folate-modified prodrugs; nanoparticles; and liposomes.

13. A method comprising: measuring expression levels of at least one gene product of a cGMP-related phosphodiesterase gene selected from the group of phosphodiesterase type 5, phosphodiesterase type 6, and phosphodiesterase type 9, wherein expression levels of the at least one gene product are measured in a renal test sample obtained from a subject.

14. The method of claim 13, wherein the renal test sample is a renal cell sample or renal tissue sample.

15. The method of claim 13, further comprising comparing the expression levels of the at least one gen product against a control expression value, wherein the control expression value is an average expression value of the measured at least one gene product of a cGMP-related phosphodiesterase gene in a population of healthy subjects.

16. The method of claim 15, wherein the population is of a size selected from the group consisting of: an individual subject; at least 5 subjects; at least 10 subjects; at least 20 subjects; at least 50 subjects; and at least 100 subjects.

17. The method of claim 15, wherein levels of phosphodiesterase type 5, phosphodiesterase type 6, and phosphodiesterase type 9 gene expression are determined to be significantly higher than those found in renal test samples from a population of healthy subjects when $p<0.05$ as determined by t-test.

18. The method of claim 13, wherein gene expression is determined using quantitative RT-PCR analysis or microarray analysis.

19. The method of claim 2, wherein the at least one compound is selected from the group consisting of: a pharmaceutically effective derivative of sildenafil; aildenafil; tadalafil; vardenafil; udenafil; avanafil; lodenafil; mirodenafil; dipyridamole; icariin; zaprinast; PF-04447943; or BAY 73-6691.

20. The method of claim 2, wherein the at least one compound is associated with a kidney-targeted drug delivery system.

* * * * *